US008617573B2

(12) United States Patent
Chapman et al.

(10) Patent No.: US 8,617,573 B2
(45) Date of Patent: Dec. 31, 2013

(54) BOTULINUM NEUROTOXIN B RECEPTORS AND USE THEREOF

(75) Inventors: Edwin Raymond Chapman, Madison, WI (US); Min Dong, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/281,501

(22) Filed: Oct. 26, 2011

(65) Prior Publication Data

US 2012/0082672 A1    Apr. 5, 2012

Related U.S. Application Data

(62) Division of application No. 10/695,577, filed on Oct. 28, 2003, now abandoned.

(60) Provisional application No. 60/422,951, filed on Oct. 31, 2002, provisional application No. 60/498,128, filed on Aug. 27, 2003.

(51) Int. Cl.
| | | |
|---|---|---|
| *A61K 39/00* | (2006.01) | |
| *A61K 39/38* | (2006.01) | |
| *A61K 39/02* | (2006.01) | |
| *A61K 39/08* | (2006.01) | |
| *A61K 38/00* | (2006.01) | |
| *A61K 38/16* | (2006.01) | |
| *A61K 38/10* | (2006.01) | |
| *A61P 25/00* | (2006.01) | |
| *A61P 3/04* | (2006.01) | |

(52) U.S. Cl.
USPC .................. 424/247.1; 424/184.1; 424/190.1; 424/236.1; 514/17.7; 514/21.2; 514/21.3; 514/21.4

(58) Field of Classification Search
None
See application file for complete search history.

(56) References Cited

U.S. PATENT DOCUMENTS

| | | | | |
|---|---|---|---|---|
| 7,846,722 | B2 * | 12/2010 | Williams et al. | 435/325 |
| 7,985,554 | B2 * | 7/2011 | Chapman et al. | 435/7.1 |
| 8,022,172 | B2 * | 9/2011 | Williams et al. | 530/300 |
| 8,067,231 | B2 * | 11/2011 | Fernandez-Salas et al. | 435/325 |
| 8,137,924 | B2 * | 3/2012 | Chapman et al. | 435/7.32 |
| 8,450,277 | B2 * | 5/2013 | Chapman et al. | 514/17.7 |
| 2004/0191887 | A1 * | 9/2004 | Chapman et al. | 435/252.3 |
| 2006/0068485 | A1 * | 3/2006 | Hu et al. | 435/252.3 |
| 2011/0223173 | A1 * | 9/2011 | Chapman et al. | 424/139.1 |
| 2012/0082672 | A1 * | 4/2012 | Chapman et al. | 424/139.1 |

FOREIGN PATENT DOCUMENTS

| | | | |
|---|---|---|---|
| WO | WO 2007/044115 | A2 * | 4/2007 |
| WO | WO 2013/011055 | A1 * | 1/2013 |

OTHER PUBLICATIONS

Dong et al, JCB, Sep. 29, 2003, 162/7:1293-1303.*
Dong et al, JCB, Dec. 31, 2007, 179/7:1511-1522.*
Chai et al, Nature, Dec. 21/28, 2006, vol. 444:1096-1100.*
GenBank Accession No. M64488, 1991.
GenBank Accession No. Q8N910, 2004.
GenBank Accession No. BAA95588, 2000.
PCT, International Search Report, PCT/US03/34348, Jul. 15, 2005.
Canadian Intellectual Property Office, Official Action, CA 2,504,532, Nov. 24, 2009.
Applicant, Response to Nov. 24, 2009 Official Action, CA 2,504,532, May 21, 2010.
Canadian Intellectual Property Office, Official Action, CA 2,504,532, Dec. 20, 2010.
Applicant, Response to Dec. 20, 2010 Official Action, CA 2,504,532, Jun. 20, 2011.
Canadian Intellectual Property Office, Official Action, CA 2,504,532, Feb. 13, 2012.
European Patent Office, Examination Report, EP 03816739.1, Sep. 25, 2007.
Applicant, Response to Sep. 25, 2007 Examination Report, EP 03816739.1, Apr. 3, 2008.
European Patent Office, Examination Report, EP 03816739.1, Aug. 21, 2008.
Applicant, Response to Aug. 21, 2008 Examination Report, EP 03816739.1, Mar. 2, 2009.
Israel Patent Office, Official Action, IL 167943, Aug. 21, 2008.
Applicant, Memorandum in Response to Aug. 21, 2008 Official Action, IL 167943, Mar. 8, 2009.
Israel Patent Office, Official Action, IL 167943, Jul. 23, 2000.
Israel Patent Office, Official Action, IL 167943, Apr. 11, 2010.
Applicant, Memorandum in Response to Apr. 11, 2010 Official Action, IL 167943, Aug. 4, 2010.
Japanese Patent Office, Official Action, JP 2005-507928, Nov. 4, 2008.
Applicant, Response to Nov. 4, 2008 Official Action, JP 2005-507928, May 7, 2009.
Japanese Patent Office, Official Action, JP 2005-507928, Jul. 1, 2009.
Applicant, Appeal Brief, JP 2005-507928, Nov. 25, 2009.
Japanese Patent Office, Official Action, JP 2005-507928, Jan. 25, 2010.
Applicant, Response to Jan. 25, 2010 Official Action, JP 2005-507928, Jul. 26, 2010.
Japanese Patent Office, Official Action, JP 2005-507928, Oct. 7, 2011.

(Continued)

*Primary Examiner* — Nita M Minnifield
(74) *Attorney, Agent, or Firm* — Quarles & Brady LLP

(57) ABSTRACT

It is disclosed here that synaptotagmin I (syt I) and synaptotagmin II (syt II) are the cellular receptors for botulinum neurotoxin B (BoNT/B) that mediate the cellular entry and toxicity of BoNT/B. The BoNT/B binding domains of syt I and II are also disclosed. While syt I needs gangliosides for BoNT/B binding, syt II can bind to BoNT/B in the absence of gangliosides. Various nucleic acids and polypeptides that relate to the BoNT/B binding domain of syt I or II are disclosed. Further disclosed are methods of reducing BoNT/B toxicity, methods of identifying agents that can block the binding between BoNT/B and syt I or II, methods of identifying agents that can bind to the BoNT/B binding domain of syt I or II, methods of detecting BoNT/B or *Clostridium botulinum* and kits for use thereof.

13 Claims, 9 Drawing Sheets

(56) References Cited

OTHER PUBLICATIONS

United States Patent and Trademark Office, Office Action, U.S. Appl. No. 10/695,577, Jun. 6, 2005.
Applicant, Response to Restriction Requirement, U.S. Appl. No. 10/695,577, Sep. 2, 2005.
United States Patent and Trademark Office, Office Action Summary and Detailed Action, U.S. Appl. No. 10/695,577, Dec. 6, 2005.
Applicant, Response to Dec. 6, 2005 Office Action, U.S. Appl. No. 10/695,577, Feb. 8, 2006.
United States Patent and Trademark Office, Office Action Summary and Detailed Action, U.S. Appl. No. 10/695,577, May 5, 2006.
Applicant, Response to May 5, 2006 Office Action, U.S. Appl. No. 10/695,577, Aug. 2, 2006.
United States Patent and Trademark Office, Office Action Summary and Final Action, U.S. Appl. No. 10/695,577, Nov. 3, 2006.
Applicant, Response to Nov. 3, 2006 Final Office Action, U.S. Appl. No. 10/695,577, Feb. 27, 2007.
United States Patent and Trademark Office, Office Action Summary and Detailed Action, U.S. Appl. No. 10/695,577, Jun. 19, 2007.
Applicant, Response to Jun. 19, 2007 Office Action, U.S. Appl. No. 10/695,577, Sep. 17, 2007.
United States Patent and Trademark Office, Office Communication, U.S. Appl. No. 10/695,577, Nov. 26, 2007.
Applicant, Response to Notice to Comply with Requirements for Patent Applications Containing Nucleotide Sequence and/or Amino Acid Sequence Disclosures, U.S. Appl. No. 10/695,577, Dec. 3, 2007.
United States Patent and Trademark Office, Office Action Summary and Final Action, U.S. Appl. No. 10/695,577, Feb. 19, 2009.
Applicant, Amendment Accompanying Request for Continued Examination (Response to Feb. 19, 2009 Final Office Action), U.S. Appl. No. 10/695,577, Aug. 17, 2009.
United States Patent and Trademark Office, Office Action Summary and Detailed Action, U.S. Appl. No. 10/695,577, Oct. 29, 2009.
Applicant, Response to Oct. 29, 2009 Non-Final Office Action, U.S. Appl. No. 10/695,577, Mar. 23, 2010.
United States Patent and Trademark Office, Office Action Summary and Final Action, U.S. Appl. No. 10/695,577, Jun. 30, 2010.
Applicant, Response to Jun. 30, 2010 Final Office Action, U.S. Appl. No. 10/695,577, Nov. 30, 2010.
United States Patent and Trademark Office, Office Action Summary and Detailed Action, U.S. Appl. No. 10/695,577, Apr. 29, 2011.
Applicant, Response to Apr. 29, 2011 Non Final Office Action, U.S. Appl. No. 10/695,577, Oct. 25, 2011.
Bai, et al., Membrane-embedded Synaptotagmin Penetrates cis or trans Target Membranes and Clusters via a Novel Mechanism, Journal of Biological Chemistry, 2000, 275(33):25427-25435.
Cameron, Recent Advances in Transgenic Technology, Molecular Biotechnology, 1997, 7:253-265.
Chapman, Synaptotagmin: A Ca2+ Sensor That Triggers Exocytosis?, Nature Reviews Molecular Cell Biology, 2002, 3:498-508.
Chapman, et al., A Novel Function for the Second C2 Domain of Synaptotagmin, Journal of Biological Chemistry, 1996, 271(10):5844-5849.
Creighton, Proteins: Structures and Molecular Principles, 1984, pp. 314-315.
Creighton, Protein Structure: A Practical Approach, 1989, pp. 184-186.
Dememes, et al., Efferent Function of Vestibular Afferent Endings? Similar Localization of N-Type Calcium Channels, Synaptic Vesicle and Synaptic Membrane-Associated Proteins, Neuroscience, 2000, 98(2):377-384.
Dong, et al., Synaptotagmins I and II Mediate Entry of Botulinum Neurotoxin B Into Cells, Journal of Cell Biology, 2003, 162(7):1293-1303.
Fukuda, et al., Inositol-1,3,4,5-tetrakisphosphate Binding to C2B Domain of IP4BP/Synaptotagmin II, Journal of Biological Chemistry, 1994, 269(46):29206-29211.

Fukuda, et al., Mechanism of the SDS-Resistant Synaptotagmin Clustering Mediated by the Cysteine Cluster at the Interface Between the Transmembrane and Spacer Domains, Journal of Biological Chemistry, 2001, 276 (43):40319-40325.
Fukuda, et al., Synaptotagmin IX Regulates Ca2+-dependent Secretion in PC12 Cells, Journal of Biological Chemistry, 2002, 277(7):4601-4604.
Fukuda, et al., Distinct Self-Oligomerization Activities of Synaptotagmin Family, Journal of Biological Chemistry, 2000, 275(36):28180-28185.
Geppert, et al., Synaptotagmin II, A Novel Differentially Distributed Form of Synaptotagmin, Journal of Biological Chemistry, 1991, 266(21):13548-13552.
Greenspan, et al., Defining Epitopes: It's Not As Easy As It Seems, Nature Biotechnology, 1999, 17:936-937.
Gut, et al., Expression and Localisation of Synaptotagmin Isoforms in Endocrine B-Cells: Their Function in Insulin Exocytosis, Journal of Cell Science, 2001, 114:1709-1716.
Hammer, et al., Spontaneous Inflammatory Disease in Transgenic Rates Expressing HLA-B27 and Human B2m: An Animal Model of HLA-B27-Associated Human Disorders, Cell, 1990, 63:1099-1112.
Houdebine, Production of Pharmaceutical Proteins from Transgenic Animals, Journal of Biotechnology, 1994, 34:269-287.
Juzans, et al., Synaptotagmin II Immunoreactivity in Normal and Botulinum Type-A Treated Mouse Motor Nerve Terminals, Pflugers Arch—Eur. J. Physiol., 1996, 431(Suppl):R283-R284.
Kappel, et al., Regulating Gene Expression in Transgenic Animals, Current Opinion in Biotechnology, 1992, 3:548-553.
Kozaki, et al. Gaglioside GT1b as a Complementary Receptor Component for *Clostridium botulinum* Neurotoxins, Microbial Pathogenesis, 1998, 25:91-99.
Lewis, et al., The Transmembrane Domain of Syntaxin 1A Is Critical for Cytoplasmic Domain Protein-Protein Interactions, Journal of Biological Chemistry, 2001, 276(18)15458-15465.
Li, et al. Isolation of Synaptotagmin as a Receptor for Types A and E Botulinum Neurotoxin and Analysis of Their Comparative Binding Using a New Microtiter Plate Assay, Journal of Natural Toxins, 1998, 7(3):215-226.
Littleton, et al., Synaptotagmin Controls and Modulates Synaptic-Vesicle Fusion in a Ca2+-dependent Manner, Trends Neurosci., 1995, 18:177-183.
Matthew, et al., Identification of a Synaptic Vesicle-Specific Membrane Protein with a Wide Distribution in Neuronal and Neurosecretory Tissue, Journal of Cell Biology, 1981, 91:257-269.
Matteoli, et al., Exo-endocytotic Recycling of Synaptic Vesicles in Developing Processes of Cultured Hippocampal Neurons, Journal of Cell Biology, 1992, 117(4):849-861.
Mullins, et al., Expression of the DBA/2J Ren-2 Gene in the Adrenal Gland of Transgenic Mice, EMBO Journal, 1989, 8(13):4065-4072.
Mullins, et al., Fulminant Hypertension in Transgenic Rats Harbouring the Mouse Ren-2 Gene, Nature, 1990, 344:541-544.
Mullins, et al., Transgenesis in Nonmurine Species, Hypertension, 1993, 22:630-633.
Mullins, et al., Perspectives Series: Molecular Medicine in Genetically Engineered Animals, J. Clin. Invest., 1996, 98 (11)(Suppl):S37-S40.
Niemann, Transgenic Farm Animals Get Off the Ground, Transgenic Research, 1998, 7:73-75.
Nishiki, et al., Identification of Protein Receptor for *Clostridium botulinum* Type B Neurotoxin in Rat Brain Synaptosomes, Journal of Biological Chemistry, 1994, 269(14):10498-10503.
Nishiki, et al., The High-Affinity Binding of Clostridium Botulinum Type B Neurotoxin to Synaptotagmin II Associated with Gangliosides GT1b/GD1a, FEBS Letters, 1996, 378:253-257.
Nishiki, et al., Binding of Botulinum Type B Neurotoxin to Chinese Hamster Ovary Cells Transfected with Rat Synaptotagmin II cDNA, Neuroscience Letters, 1996, 208:105-108.
Nosoh, et al., Protein Stability and Stabilization Through Protein Engineering, 1991, Chapter 7, p. 197, Second Paragraph.
Osborne, et al., Calcium-Dependent Oligomerization of Synaptotagmins I and II, Journal of Biological Chemistry, 1999, 274(1):59-66.

(56) References Cited

OTHER PUBLICATIONS

Overbeek, Transgenic Animal Technology, A Laboratory Handbook, 1994, pp. 96-98.

Perin, et al., Phospholipid Binding by a Synaptic Vesicle Protein Homologous to the Regulatory Region of Protein Kinase C, Nature, 1990, 345:260-263.

Schiavo, et al., Tetanus and Botulinum-B Neurotoxins Block Neurotransmitter Release by Proteolytic Cleavage of Synaptobrevin, Nature, 1992, 359:832-835.

Schiavo, et al., Synaptotagmins: More Isoforms Than Functions?, Biochemical and Biophysical Research Communications, 1998, 248:1-8.

Shoji-Kasai, et al., Neurotransmitter Release from Synaptotagmin-Deficient Clonal Variants of PC12 Cells, Science, 1992, 256(5065):1820-1823.

Taurog, et al., HLA-B27 in Inbred and Non-Inbred Transgenic Mice, Journal of Immunology, 1988, 141:4020-4023.

Wall, Transgenic Livestock: Progress and Prospects for the Future, Theriogenology, 1996, 45:57-68.

Wang, et al., Synaptotagmin Modulation of Fusion Pore Kinetics in Regulated Exocytosis of Dense-Core Vesicles, Science, 2001, 294:1111-1115.

GenBank Accession No. P24506, 1991.
GenBank Accession No. P24505, 1991.
GenBank Accession No. P47191, 1993.
GenBank Accession No. NP_005630, 1991.
GenBank Accession No. X52772, 1990.
GenBank Accession No. D37793, 1994.
GenBank Accession No. D37792, 1994.

\* cited by examiner

BOTULINUM NEUROTOXIN B RECEPTORS AND USE THEREOF

CROSS-REFERENCE TO RELATED APPLICATIONS

This application is a divisional application of U.S. patent application Ser. No. 10/695,577, filed on Oct. 28, 2003, now abandoned which claims the benefit of U.S. Provisional Application No. 60/422,951, filed on Oct. 31, 2002, and U.S. Provisional Application No. 60/498,128, filed on Aug. 27, 2003, all of which are herein incorporated by reference.

STATEMENT REGARDING FEDERALLY SPONSORED RESEARCH OR DEVELOPMENT

This invention was made with government support under MH61876 and GM56827 awarded by the National Institutes of Health. The government has certain rights in the invention.

BACKGROUND OF THE INVENTION

Clostridial neurotoxins (CNT) are the most toxic substances known. There are eight related toxins—seven botulinum neurotoxins (BoNT/A-G) and tetanus neurotoxin (TeNT) (Schiavo et al., 2000; Simpson, 1981). BoNTs can cause botulism disease and are potential biological weapons (Arnon et al., 2001; Mahant et al., 2000). Each of the BoNT and TeNT is composed of a heavy and light chain; the heavy chain mediates binding to the surface of specific nerve terminals. Once internalized via endocytosis, the light chain is translocated from the lumen of the vesicle into the cytoplasm where it functions as a zinc-dependent protease (Schiavo et al., 2000). The light chain cleaves one or more components of a conserved membrane fusion complex composed of syntaxin, SNAP-25 and synaptobrevin (syb), thereby blocking exocytosis (Blasi et al., 1993a; Blasi et al., 1993b; Schiavo et al., 1992; Schiavo et al., 1993). Because of their ability to selectively disrupt $Ca^{2+}$-triggered exocytosis, the CNTs have emerged as important tools for the study of membrane fusion and synaptic transmission (Jahn and Niemann, 1994).

The first step in the action of CNTs involves binding to receptors on the surface of neurons. Current evidence suggests that the receptors are composed of gangliosides and proteins that cooperate to form high affinity toxin binding sites. Alternatively, gangliosides may constitute relatively low-affinity toxin binding sites that serve to capture CNTs to facilitate interactions with cell surface receptor proteins (Montecucco, 1986; Nishiki et al., 1996a). Gangliosides are ubiquitous glycosphingolipids in the outer leaflet of plasma membranes. They are classified according to the number and position of sialic acids present in their head groups. Polysialiogangliosides, which are present almost exclusively in neurons and neuroendrocrine cells, bind to CNTs with the greatest avidity (Halpern and Neale, 1995). While a protein component is also clearly involved in toxin-cell recognition, at present, a protein that mediates toxin entry has not been identified (Schiavo et al., 2000).

Biochemical studies have led to the identification of a handful of CNT binding proteins. In most case, these binding proteins do not appear to function as receptors that mediate entry of the toxins. For example, BoNT/A,B,E and TeNT were reported to bind synapsin I and adducin, respectively (Schengrund et al., 1996; Schengrund et al., 1993; Schengrund et al., 1992). Since neither of these proteins are exposed to the outside surface of cells, they are unlikely to function as cell surface receptors. TeNT was reported to bind Thy-1, a GPI-anchored plasma membrane protein. However, neurons from mice lacking Thy-1 are still sensitive to TeNT, suggesting that Thy-1 is not essential for TeNT entry into cells (Herreros et al., 2001).

Synaptotagmins (syt) I and II (Nishiki et al., 1994) are homologous synaptic vesicle membrane proteins thought to function as $Ca^{2+}$-sensors for exocytosis (Chapman, 2002; Schiavo et al., 1998). Syt I and II were reported to bind BoNT/B in the presence of gangliosides; the dissociation constant for the syt I.BoNT/B complex was 2.3 nM and the dissociation constant for syt II.BoNT/B was 0.23 nM (Nishiki et al., 1996a). High affinity binding of BoNT/B to fibroblasts was reconstituted by expression of syt II and incorporation of exogenous gangliosides into surface membranes. However, binding did not result in the cleavage of the BoNT/B target protein, syb II, that had been co-expressed with syt II, indicating that the toxin was not internalized (Nishiki et al., 1996b). Although biochemical studies clearly established that syt binds to BoNT/B, evidence that binding mediates entry into cells is lacking. Thus, whether this interaction has any functional role remains unknown. More recently, BoNT/A and E have also been reported to bind syt I, albeit in a ganglioside independent manner (Li and Singh, 1998).

Syt II is a 422-amino acid protein that contains a luminal domain (a.a. 1-60), a transmembrane domain (a.a. 61-87) and a cytoplamic domain (a.a. 88-422). The cytoplasmic domain contains two C2 domains: C2A (a.a. 88-267) and C2B (a.a. 275-422) linked by a linker region (a.a. 268-274).

Determining whether any of the above proteins, or perhaps other proteins, serve as the BoNT receptor will be extremely useful for designing molecules that can reduce or completely inhibit BoNT toxicity. For the same reason, once a receptor is identified, it is important to map the BoNT binding domain because polypeptides containing the domain and peptidomimics thereof can be used to compete with the receptor for BoNT binding, thereby reducing or completely inhibiting BoNT toxicity.

BRIEF SUMMARY OF THE INVENTION

The present invention is based on the identification of syt I and II as BoNT/B receptors as well as the identification of the BoNT/B binding domains on syt I and II.

In one aspect, the present invention relates to an isolated nucleic acid that contains a coding sequence either for the BoNT/B binding domain of syt I or II of the rat, mouse or human species or for an amino acid sequence that is at least 70%, 80%, 90% or 95% identical to the foregoing BoNT/B binding domain. An isolated nucleic acid having a nucleotide sequence that is at least 80% identical to the coding sequence of the BoNT/B binding domain of syt I or II of the rat, mouse or human species or hybridizes to the coding sequence under stringent or moderately stringent hybridization conditions is also within the scope of the invention. The nucleic acid of the present invention can be provided in a vector or host cell and operably linked to a non-native expression control sequence. For human syt I and II, the BoNT/B binding domains are amino acids 33-53 and 37-57, respectively. For rat or mouse syt I and II, the BoNT/B binding domains are amino acids 32-52 and 40-60, respectively.

In another aspect, the present invention relates to an isolated polypeptide that contains either the BoNT/B binding domain of syt I or II of the rat, mouse or human species or an amino acid sequence that is at least 70%, 80%, 90% or 95% identical to the foregoing domain. An antibody specific either to the BoNT/B binding domain of syt I or II of the rat, mouse or human species or to an amino acid sequence that is at least 70%, 80%, 90% or 95% identical to the foregoing domain is also within the scope of the present invention.

Other aspects of the invention relate to methods of reducing BoNT/B toxicity, methods of identifying agents that can block the binding between BoNT/B and syt I or II, methods of identifying agents that can bind to the BoNT/B binding domain of syt I or II, and methods of detecting BoNT/B or *Clostridium botulinum*.

BRIEF DESCRIPTION OF THE FIGURES

FIG. 2 shows mapping of the BoNT/B binding site within the luminal domain of syt II. A) Binding assays were carried out as in FIG. 1A, using the indicated syt II truncation mutants. The upper panel shows a schematic of the truncation mutants where (+) denotes binding and (−) denotes lack of binding. B) Sequence of the amino terminus of syt I and II. The underlined region (residues 40-60 in syt II; residues 32-52 in syt I) is critical for binding BoNT/B; the asterisks indicate sequence differences. The TMD is boxed. C) Upper panel—A peptide, P21, corresponding to residues 40-60 of syt II plus a C-terminal cys residue was conjugated to agarose beads and used to pull-down toxin as described in (A); a scrambled peptide, P21S (IKMNDAEFFGKSNFQEKLE-KEC, SEQ ID NO:5), served as a negative control. Lower panel—P21, but not P21S, blocked the interaction between BoNT/B and the 1-87 fragment of syt II. Binding assays were carried out as in (A), but as a function of the indicated P21 or P21S concentration.

FIG. 5 shows that syt II fragments that contain the BoNT/B binding site block binding and entry of the toxin into syt II⁺ cells. A) Cells were decorated with BoNT/B as in FIG. 3A in the absence or presence of the indicated syt II fragments. Syt II 1-267 and 61-267 were purified using a his6-tag at the amino terminus and syt II 1-87 was purified as a GST-fusion protein and eluted from beads using glutathione. Syt fragments 1-267 and 1-87, as well as the P21 peptide (residues 40-60), blocked binding; 61-267 and P21S had no effect. The syt II 1-267 and 61-267 fragments form aggregates bound to cell membranes (Bai et al., 2000) as visualized with an anti-his6 antibody in the bottom panel; for syt II 1-267, these aggregates also contained BoNT/B. The final concentrations of recombinant protein and peptides in the media were 960 nM and 10 µM, respectively; the final concentration of BoNT/B was 30 nM. B) Syt II⁺ PC12 cells (clone No. 1) were treated with 30 nM BoNT/B that was premixed with the indicated concentration of the syt II 1-267 fragment in the absence (upper panel) or presence of gangliosides (25 µg/ml; lower panel) for 48 hrs. Samples were analyzed by immunoblotting as described in FIG. 3B. Cleavage of syb II was inhibited by the 1-267 fragment of syt II; inclusion of gangliosides increased the ability of the syt fragment to block cleavage of syb II. Fragment 61-267 had no effect. C) Experiments were carried out as in (A), but using the P21 or P21S peptides.

FIG. 7 shows protection of mice from BoNT/B toxicity using fragments of syt II. A) Specific toxicity of BoNT/B in female mice was determined by an intravenous time-to-death assay (Boroff and Fleck, 1966). The standard curve was used to convert time-to-death (min) to $LD_{50}$/ml. The resultant $LD_{50}$/ml values were used to calculate % neutralization of toxicity using the expression: $1-[LD_{50}/ml (+syt\ II\ fragment)/LD_{50}/ml (-syt\ II\ fragment)] \times 100$, where (+syt II fragment) refers to samples that contain toxin, gangliosides and recombinant proteins and (-syt II fragment) samples were composed of toxin and gangliosides only. B) The indicated syt fragments (5 μM) were pre-mixed with gangliosides (250 μg/ml) and BoNT/B concentrations that lie in the linear range of the standard curve in panel A (i.e. $10^5$-$10^6$ $LD_{50}$/ml) for 10 min at room temperature, and injected intravenously (100 μl) into mice. Percent neutralization was determined as described in panel A. In all the in vivo experiments, the indicated concentrations correspond to the initial concentration prior to i.v. injection; the dilution factor in the circulatory system is about 1:10. C) Experiments were carried out as described in panel B, but as a function of the syt II 1-267 or 1-87 concentration. D) Pre-injection of gangliosides (250 μg/ml) plus syt II 1-267 (17 μM) or 1-87 (20 μM) mixtures protects mice from subsequent exposure to BoNT/B. Experiments were carried out as in (B), except that toxin was injected 1 min after injection of the receptor complex. Note: in panels (B-D), each data point represents the average of at least triplicate determinations; error was within +/−10%.

DETAILED DESCRIPTION OF THE INVENTION

Figure 1:
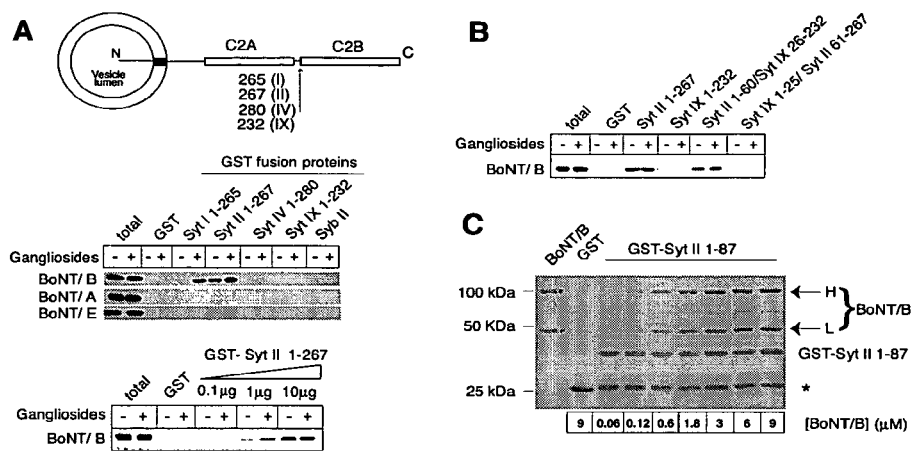
FIG. 1 shows interactions between syt isoforms and BoNT/A, B and E. A) Upper panel, schematic diagram of the syt constructs used in the GST-pull down experiments. To facilitate purification, all syt constructs lacked a C2B domain; the arrow indicates the C-terminus of the truncated syts. The transmembrane domain (TMD) is indicated by a black rectangle. Middle panel, GST or the indicated GST-fusion proteins were incubated with 30 nM BoNT/B, A and E, either with (+; 25 µg/ml) or without (−) gangliosides in 100 µl of TBS. Seventeen percent of the bound materials were analyzed by SDS-PAGE and immunoblotting using anti-CNT polyclonal antibodies. "Total" corresponds to 80 ng of toxin. In the lower panel, the amount of fusion protein was varied as indicated. B) Binding assays were carried out as in (A). N-terminal fragments of syt II and IX served as positive and negative controls, respectively, and two chimeric constructs, in which the luminal domains of syt II and IX were swapped, were tested for toxin binding activity. C) Binding assays were carried out as in (A) using immobilized syt II 1-87 and the indicated concentrations of BoNT/B. Bound toxin was visualized by staining with Coomassie blue; binding was stoichiometric at saturation. The heavy chain (H) of BoNT/B runs at 100 kDa, the light chain (L) runs at 50 kDa. The asterisk denotes a proteolytic fragment of GST-syt II 1-87.

It is disclosed here that among many proteins that can bind BoNT/B, syt I and II are the BoNT/B receptors that mediate the toxin's cellular entry and neuro-toxicity. The BoNT/B binding domain and the ganglioside binding domain of syt I and II are also disclosed. While syt I needs both the BoNT/B and ganglioside binding domains as well as gangliosides for BoNT/B binding, syt II only needs its BoNT/B binding domain to bind BoNT/B. The ganglioside binding domain along with gangliosides can enhance the binding between BoNT/B and syt II. The disclosure here provides new prevention and treatment strategies for BoNT/B toxicity and botulism disease. The disclosure here also provides new tools for identifying agents that can be used to reduce binding between BoNT/B and syt I or II and hence BoNT/B cellular entry and toxicity.

It is known in the art that the function and amino acid sequences of syt I and II are conserved across animal species. Although the disclosure here is based on the findings with rat syt I and mouse syt II, the findings apply to all animal species that have conserved syt I or II BoNT/B or ganglioside binding domains with regard to the corresponding domains of rat syt I and mouse syt II. For example, for the syt I and II BoNT/B binding domains and their ganglioside binding domains, the human, rat and mouse amino acid sequences are at least 94% identical. As additional examples, the syt I BoNT/B binding domains of chicken (GenBank Accession No. P47191) and *Discopyge ommata* (GenBank Accession No. P24506 and P24505) are 80% and 78% identical to the rat BoNT/B binding domain, respectively, and the syt I ganglioside binding domain of *Discopyge ommata* is about 80% identical to that of rat syt I. It is expected that for a BoNT/B binding domain or a ganglioside binding domain of either syt I or syt II of the human, rat and mouse species, any polypeptide that is at least 70% identical to one of these domains over the entire length of the domains will retain their functions in BoNT/B and gangliosides binding.

The mouse and rat syt I nucleotide sequences are provided as SEQ ID NO:1 and 3 (GenBank Accession No. D37792 and X52772), respectively, and the corresponding amino acid sequences are provided as SEQ ID NO:2 and 4. The mouse and rat syt II nucleotide sequences are provided as SEQ ID NO:6 and 8 (GenBank Accession No. D37793 and M64488), respectively, and the corresponding amino acid sequences are provided as SEQ ID NO:7 and 9. The human syt I and syt II amino acid sequences are provided as SEQ ID NO:5 and 10 (GenBank Accession No. NP_005630 and Q8N9I0), respectively. For murine (rat or mouse) syt I and II, the BoNT/B binding domains are amino acids 32-52 and 40-60, respectively, and the ganglioside binding domains are amino acids 53-79 and 61-87, respectively. For human syt I and II, the BoNT/B binding domains are amino acids 33-53 and 37-57, respectively, and the ganglioside binding domains are amino acids 54-80 and 58-84, respectively. The amino acid sequences of syt I and II of some other animal species are available in the art and a skilled artisan can readily determine the BoNT/B and ganglioside binding domains thereof using any alignment program or other methods based on the disclosure here.

Polypeptides, Nucleic Acids, Vectors and Host Cells that Contain the BoNT/B Binding Domain of syt I or II The term "isolated polypeptide" or "isolated nucleic acid" used herein means a polypeptide or nucleic acid isolated from its natural environment or prepared using synthetic methods such as those known to one of ordinary skill in the art. Complete purification is not required in either case. The polypeptides and nucleic acids of the invention can be isolated and purified from normally associated material in conventional ways such that in the purified preparation the polypeptide or nucleic acid is the predominant species in the preparation. At the very least, the degree of purification is such that the extraneous material in the preparation does not interfere with use of the polypeptide or nucleic acid of the invention in the manner disclosed herein. The polypeptide or nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of clones, e.g., as these occur in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine.

In one aspect, the present invention relates to an isolated polypeptide having an amino acid sequence that is at least 70%, 80%, 90% or 95% identical to that of the BoNT/B binding domain of syt I or II of the rat, mouse or human species. Specifically excluded from the polypeptide of the present invention is one that contains full length syt I or II. In a preferred embodiment, the isolated polypeptide has an amino acid sequence selected from amino acids 32-52 of SEQ ID NO:2 or 4, amino acids 33-53 of SEQ ID NO:5, amino acids 40-60 of SEQ ID NO:7 or 9, or amino acids 37-57 of SEQ ID NO:10.

Optionally, the isolated polypeptide of the present invention further contains an amino acid sequence that is at least 70%, 80%, 90% or 95% identical to the ganglioside binding domain of syt I or II of the rat, mouse or human species. The BoNT/B binding domain and the ganglioside binding domain on the same polypeptide do not have to be from the same protein and species. For example, a polypeptide of the present invention can contain a BoNT/B binding domain of syt I of one species and a ganglioside binding domain of syt II of another species. The ganglioside binding domains of syt I and II are the same as the transmembrane domains. In a preferred embodiment of the present invention, a polypeptide of the present invention further contains an amino acid sequence selected from amino acids 53-79 of SEQ ID NO:2 or 4, amino acids 54-80 of SEQ ID NO:5, amino acids 61-87 of SEQ ID NO:7 or 9, or amino acids 58-84 of SEQ ID NO:10.

Examples of the polypeptides of the present invention include but are not limited to those that contain amino acids 32-52 or 32-79 of mouse or rat syt I, amino acids 33-53 or 33-80 of human syt I, amino acids 40-60, 1-61, 1-87, 40-87, 40-267 or 1-267 of mouse or rat syt II, amino acids 37-57, 1-57, 1-84, 37-84, 37-264 or 1-264 of human syt II, or a syt I or II fragment in other animal species that corresponds to any of the foregoing syt I and II fragments. It is understood that substitutions such as conservative substitutions can be introduced into non-critical amino acid positions and this will not materially affect the function of the BoNT/B binding domain of syt I or II. An isolated polypeptide that contains the BoNT/B binding domain of syt I or II with such substitutions is within the scope of the present invention. The isolated polypeptide of the invention can include one or more amino acids at either or both N-terminal and C-terminal ends of the BoNT/B binding domain of syt I or II, where the additional amino acid(s) do not materially affect the function of the domain (binding BoNT/B). Any additional amino acids can, but need not, have advantageous use in purifying, detecting, or stabilizing the polypeptide.

In order to improve the stability and/or binding properties of a polypeptide, the molecule can be modified by the incorporation of non-natural amino acids and/or non-natural chemical linkages between the amino acids. Such molecules are called peptidomimics (H. U. Saragovi et al. Bio/Technology (1992), Vol 10, 773-778; S. Chen et al., Proc. Natl. Acad. Sci. USA (1992) Vol 89, 5872-5876). The production of such compounds is restricted to chemical synthesis. It is understood that a polypeptide of the present invention can be modified into peptidomimics without abolishing its function. This can be readily achieved by a skilled artisan.

In another aspect, the present invention relates to an isolated nucleic acid containing a coding polynucleotide or its complement wherein the coding polynucleotide has an uninterrupted coding sequence that encodes a polypeptide of the invention as set forth above. A nucleic acid containing a polynucleotide that can hybridize to the coding polynucleotide or its complement, under either stringent or moderately stringent hybridization conditions, is useful for detecting the coding polypeptide and thus is within the scope of the present invention. Stringent hybridization conditions are defined as hybridizing at 68° C. in 5×SSC/5×Denhardt's solution/1.0% SDS, and washing in 0.2×SSC/0.1% SDS+/−100 ng/ml denatured salmon sperm DNA at room temperature, and moderately stringent hybridization conditions are defined as washing in the same buffer at 42° C. Additional guidance regarding such conditions is readily available in the art, for example, by Sambrook et al., 1989, *Molecular Cloning, A Laboratory Manual*, Cold Spring Harbor Press, N.Y.; and Ausubel et al. (eds.), 1995, *Current Protocols in Molecular Biology*, (John Wiley & Sons, N.Y.) at Unit 2.10. A nucleic acid containing a polynucleotide that is at least 80% identical to the coding polynucleotide or its complement over the entire length of the coding polynucleotide can also be used as a probe for detecting the coding polynucleotide and is thus within the scope of the present invention. Specifically excluded from the present invention is a nucleic acid that contains a nucleotide sequence encoding full length syt I or II.

In a related aspect, any nucleic acid of the present invention described above can be provided in a vector in a manner known to those skilled in the art. The vector can be a cloning vector or an expression vector. In an expression vector, the polypeptide-encoding polynucleotide is under the transcriptional control of one or more non-native expression control sequences which can include a promoter not natively found adjacent to the polynucleotide such that the encoded polypeptide can be produced when the vector is provided in a compatible host cell or in a cell-free transcription and translation system. Such cell-based and cell-free systems are well known to a skilled artisan. Cells comprising a vector containing a nucleic acid of the invention are themselves within the scope of the present invention. Also within the scope of the present invention is a host cell having the nucleic acid of the present invention integrated into its genome at a non-native site.

Methods for Reducing BoNT/B Neuro-Toxicity

In another aspect, the present invention relates to a method for reducing BoNT/B cellular toxicity in target cells such as neurons. As a result, botulism disease can be prevented or treated. The term "reducing BoNT/B cellular toxicity" encompasses any level of reduction in BoNT/B toxicity. The BoNT/B toxicity can be reduced by reducing the syt I or syt II protein levels in target cells, by inhibiting BoNT/B-related cellular functions of syt I or II in target cells, or by reducing the binding between BoNT/B and syt I or II located on the cellular surface of target cells. The binding between BoNT/B and syt I or II can be reduced by blocking the binding between BoNT/B and its binding domains on syt I or II, or by reducing the binding between gangliosides and the ganglioside binding domains on syt I or II. A reduction in the above bindings can be readily accomplished by a skilled artisan through either blocking the bindings directly or reducing the amount of syt I, syt II or gangliosides.

Reducing Syt I and Syt II Protein Level

There are many methods by which cellular protein levels such as the levels of syt I and II can be reduced. The present invention is not limited to a particular method employed. As an example, the cellular levels of syt I and II can be reduced using antisense technology. For example, a 20-25mer antisense oligonucleotide can be directed against the 5' end of syt I or II mRNA with phosphorothioate derivatives on the last three base pairs on the 3' and 5' ends to enhance the half life and stability of the oligonucleotides. A carrier for an antisense oligonucleotide can be used. An example of a suitable carrier is cationic liposomes. For example, an oligonucleotide can be mixed with cationic liposomes prepared by mixing 1-alpha dioleylphatidylcelthanolamine with dimethldioctadecylammonium bromide in a ratio of 5:2 in 1 ml of chloroform. The solvent will be evaporated and the lipids resuspended by sonication in 10 ml of saline. Another way to use an antisense oligonucleotide is to engineer it into a vector so that the vector can produce an antisense cRNA that blocks the translation of the mRNAs encoding for syt I and II. Similarly, RNAi techniques, which are now being applied to mammalian systems, are also suited for inhibiting the expression of syt I and II. (See Zamore, *Nat. Struct. Biol.* 8:746:750 (2001), incorporated herein by reference as if set forth in its entirety).

Dominant Negative Syt I and II

In another aspect, the present invention relates to identifying a dominant negative syt I or II that can negate the effects of BoNT/B on cells that express syt I or II. A dominant negative syt I or II can be identified by introducing a mutation into a syt I or II gene, expressing the mutated syt I or II and the wild type syt I or II in the same host cell and determining the effect of the mutated syt I or II on parameters that relate to BoNT/B toxicity, which include but are not limited to susceptibility of the host cell to BoNT/B, integration of newly formed syt I or II into the host cell membrane, binding of wild type syt I or II to BoNT/B, and uptake of BoNT/B and syt I or II complex into cells. The wild type syt I or II expressed in the host cell can be the endogenous syt I or II gene or a syt I or II gene introduced into the host cell. Any dominant negative syt I or II identified is within the scope of the present invention. The identified dominant negative syt I or II can be used to negate the effect of BoNT/B toxin, which can be readily accomplished by a skilled artisan.

Blocking the Binding Between BoNT/B and Syt I or II

The identification of syt I and II as BoNT/B receptors as well as the BoNT/B binding sequences on the receptors enables those skilled in the art to block the binding between BoNT/B and its receptors through many familiar strategies. One strategy is to use monoclonal or polyclonal antibodies specific for the BoNT/B binding domains of syt I and II to block the BoNT/B binding sites on syt I and II. Since gangliosides are required for BoNT/B to bind syt I and they also enhance the binding between BoNT/B and syt II, antibodies specific for the ganglioside binding domains on syt I and II can also be used to block or reduce the binding between BoNT/B and syt I or II. Given that the amino acid sequences of the BoNT/B and ganglioside binding domains of syt I and II are disclosed here, it is well within the capability of a skilled artisan to generate monoclonal or polyclonal antibodies specific for these domains. The antibodies so generated are within the scope of the present invention.

Another strategy to block the binding between BoNT/B and syt I or II is to use a polypeptide having an amino acid sequence that is at least 70%, 80%, 90% or 95% identical to a BoNT/B binding domain of syt I or II of the rat, mouse or human species, including syt I and II themselves, to compete with syt I or II located on the cellular surface of target cells for BoNT/B binding. Preferred polypeptides of the present invention contains a BoNT/B binding domain of syt I or II of the rat, mouse or human species. To block the binding between BoNT/B and syt I or II in a specific species, a syt I or II BoNT/B binding domain of the same species or a different species can be used. Since syt I needs gangliosides to bind BoNT/B, the polypeptide that contains a syt I BoNT/B binding domain-related sequence should also contain an amino acid sequence that is at least 70%, 80%, 90% or 95% identical to a ganglioside binding domain of the rat, mouse or human species, and gangliosides should also be employed. In a preferred embodiment of the method, a ganglioside binding domain of the rat, mouse or human species is used. The ganglioside binding domain on a polypeptide of the present invention can be from either syt I or syt II and of the same or different species as the BoNT/B binding domain of syt I. Preferably, the ganglioside binding domain is that of syt I and of the same species as the BoNT/B binding domain. The employment of gangliosides is optional when the polypeptide is used for competing with syt II on target cells. Suitable polypeptides that can be used in the present invention include but are not limited to those that contain amino acids 32-79 of mouse or rat syt I, amino acids 33-80 of human syt I, amino acids 40-60, 1-61, 1-87, 40-87, 40-267, 1-267 and 1-422 of mouse or rat syt II, amino acids 37-57, 1-58, 1-84, 37-84, 37-264, 1-264 and 1-419 of human syt II, and fragments in other animal species that correspond to the foregoing syt I and II fragments. The polypeptide can be introduced into a human or nonhuman subject by administering the polypeptide directly or a vector that can express the polypeptide in the human or nonhuman subject.

Those skilled in the art understand that mutations such as substitutions, insertions and deletions can be introduced into the BoNT/B binding domains of syt I and II without abolishing their BoNT/B binding activity. Some mutations may even enhance the binding activity. A polypeptide containing such mutants can obviously be used in the method of the present invention. The syt I and II BoNT/B binding domain mutants that retain the BoNT/B binding activity can be identified by using the screening methods described below.

Identifying Agents that can Block Binding Between BoNT/B and Syt I or II

Agents that can block binding between BoNT/B and syt I or II can be screened by employing BoNT/B and a polypeptide that contains either a BoNT/B binding domain of syt I and a ganglioside binding domain of syt I or II, or a BoNT/B binding domain of syt II, under conditions suitable for BoNT/B to bind the polypeptide. Gangliosides are included when the method is used for screening for agents that can block BoNT/B-syt I binding. For BoNT/B-syt II screening, the inclusion of gangliosides and the ganglioside binding domain of syt II on the polypeptide is optional. The binding between BoNT/B and the polypeptide can be measured in the presence of a test agent and compared to that of a control that is not exposed to the test agent. A lower than control binding in the test agent group indicates that the agent can block binding between BoNT/B and syt I or II. The BoNT/B binding domain or ganglioside binding domain of syt I or II used here are that of the rat, mouse or human species. A polypeptide that contains an amino acid sequence that is at least 70%, 80%, 90% or 95% identical to the BoNT/B binding domain or ganglioside binding domain of syt I or II can also be used in the method. The preferred polypeptides for the screening assay are the BoNT/B and ganglioside binding domains of syt I and the BoNT/B binding domain of syt II.

There are many systems that a skilled artisan is familiar with for assaying the binding between BoNT/B and the BoNT/B binding domain on syt I or II. Any of these systems can be used in the screening method. Detailed experimental conditions can be readily determined by a skilled artisan. For example, the binding between BoNT/B and the polypeptide described above can be measured in vitro (cell free system). A cell culture system in which syt I or II are expressed and translocated onto the cellular membrane can also be used. For the cell culture system, in addition to the binding between BoNT/B and syt I or II, the entry of BoNT/B into the cells and a number of other parameters such as those disclosed in the examples below, can also be used as an indicator of binding between BoNT/B and syt I or II.

Any method known to one of ordinary skill in the art for measuring protein-protein interaction can be used to measure the binding between BoNT/B and the BoNT/B binding domain of syt I or II. For example, coimmunoprecipitation and affinity columns are two methods commonly used. Another method that can be used is surface plasmon resonance (SPR). SPR uses changes in refractive index to quantify binding and dissociation of macromolecules to ligands covalently linked onto a thin gold chip within a micro flow cell. This technique has been used to study protein-protein interactions in many systems, including the interactions of PA63 with EF and LF (Elliott, J. L. et al., *Biochemistry* 39:6706-6713, 2000). It provides high sensitivity and accuracy, the ability to observe binding and release in real time, and consumption of only minute quantities of protein. Besides the equilibrium dissociation constant (Kd), on- and off-rate constants (ka and kd) may also be obtained. Typically, a protein to be studied is covalently tethered to a carboxymethyl dextran matrix bonded to the gold chip. Binding of a proteinaceous ligand to the immobilized protein results in a change in refractive index of the dextran/protein layer, and this is quantified by SPR. A BIAcore 2000 instrument (Pharmacia Biotech) can be used for these measurements.

For the cell culture system, the binding of BoNT/B to syt I or II can be assayed by staining the cells, the examples of which are described in the examples below.

Identifying Agents that Bind BoNT/B Binding Domain of Syt I or II

Agents that can bind to the BoNT/B binding domain of syt I or II can be used to block the binding between BoNT/B and syt I or II. Such agents can be identified by providing a polypeptide that contains a BoNT/B binding domain of syt I or II to a test agent, and determining whether the agent binds to the BoNT/B binding domain. The BoNT/B binding domain or ganglioside binding domain of syt I or II used here are that of the rat, mouse or human species. A polypeptide that contains an amino acid sequence that is at least 70%, 80%, 90% or 95% identical to the BoNT/B binding domain of syt I or II can also be used in the method. The preferred polypeptides are the BoNT/B binding domains of syt I and syt II themselves. Optionally, agents identified by the method is further tested for the ability to block BoNT/B entry into cells or to neutralize BoNT/B toxicity. A skilled artisan is familiar with the suitable systems that can be used for the further testing. Examples of such systems are provided in the examples below.

The skilled artisan is familiar with many systems in the art for assaying the binding between a polypeptide and an agent. Any of these systems can be used in the method of the present invention. Detailed experimental conditions can be readily determined by a skilled artisan. For example, a polypeptide that contains amino acids the BoNT/B binding domain of syt I or II can be provided on a suitable substrate and exposed to a test agent. The binding of the agent to the polypeptide can be detected either by the loss of ability of the polypeptide to bind to an antibody or by the labeling of the polypeptide if the agent is labeled with radioactivity, fluorescence or other features. In another example, a polypeptide that contains the BoNT/B binding domain of syt I or II can be expressed in a host cell, and the cell is then exposed to a test agent. Next, the polypeptide can be isolated, e.g., by immunoprecipitation or electrophoresis, and the binding between the polypeptide and the agent can be determined. As mentioned above, one way to determine the binding between the polypeptide and the agent is to label the agent with radioactivity or fluorescence so that the polypeptide that binds to the agent becomes radioactive or fluorescent upon binding. If the test agent is a polypeptide, examples of specific techniques for assaying protein/protein binding as described above can also be used. It should be noted that when the BoNT/B binding domain of syt I or II used in the screening assay have flanking sequences, it may be necessary to confirm that an agent binds to the BoNT/B binding domain rather than the flanking sequences, which can be readily accomplished by a skilled artisan.

Agents that can be Screened

The agents screened in the above screening methods can be, for example, a high molecular weight molecule such as a polypeptide (including, e.g., a polypeptide containing a mutant BoNT/B binding domain of syt I or II, or a monoclonal or polyclonal antibody to the BoNT/B binding domain or the full length of syt I or II), a polysaccharide, a lipid, a nucleic acid, a low molecular weight organic or inorganic molecule, or the like.

Batteries of agents for screening are commercially available in the form of various chemical libraries including peptide libraries. Examples of such libraries include those from ASINEX (i.e. the Combined Wisdom Library of 24,000 manually synthesized organic molecules) and CHEMBRIDGE CORPORATION (i.e. the DIVERSet™ library of 50,000 manually synthesized chemical compounds; the SCREEN-Set™ library of 24,000 manually synthesized chemical compounds; the CNS-Set™ library of 11,000 compounds; the Cherry-Pick™ library of up to 300,000 compounds) and linear library, multimeric library and cyclic library (Tecnogen (Italy)). Once an agent with desired activity is identified, a library of derivatives of that agent can be screened for better molecules. Phage display is also a suitable approach for finding novel inhibitors of the interaction between BoNT/B and syt I or II.

Methods of Detecting BoNT/B or *Clostridium botulinum*

In another aspect, the present invention relates to a method of detecting BoNT/B or *Clostridium botulinum*. The method involves exposing a sample suspected of containing BoNT/B to an agent that contains a polypeptide having a BoNT/B binding domain of syt I and a ganglioside binding domain of syt I or II, or a BoNT/B binding domain of syt II, and detecting binding of the polypeptide to BoNT/B. When the BoNT/B and ganglioside binding domains of syt I are used, gangliosides are also provided in the agent. When the BoNT/B binding domain of syt II is used, the inclusion of gangliosides and the ganglioside binding domain of syt II on the polypeptide is optional. The BoNT/B binding domain or ganglioside binding domain of syt I or II used here are that of the rat, mouse or human species. A polypeptide with an amino acid sequence that is at least 70%, 80%, 90% or 95% identical to the BoNT/B binding domain or ganglioside binding domain of syt I or II can also be used in the method.

Kits

Any product of the invention described herein can be combined with one or more other reagent, buffer or the like in the form of a kit useful, e.g., for diagnostic, preventive or therapeutic purposes, in accord with the understanding of a skilled artisan.

The invention will be more fully understood upon consideration of the following non-limiting examples.

EXAMPLES

Materials and Methods

Cell Lines, Gangliosides and Toxins—

A syt I deficit (Syt I$^-$) PC12 cell line was kindly provided by Y. Shoji-Kasai and M. Takahashi (Tokyo, Japan) (Shoji-Kasai et al., 1992). A mixture of bovine brain gangliosides (18% $GM_1$, 55% $GD_{1a}$, 10% $GT_{1b}$, and 2% other gangliosides), hereafter designated as gangliosides, were obtained from Calbiochem. BoNT/A, B and E were purified as described (Dasgupta et al., 1970; Evans et al., 1986; Schmidt and Siegel, 1986).

Antibodies—

Monoclonal antibodies directed against syb II (69.1), syt I (α-syt $I_N$; 604.4, α-syt $I_C$; 41.1), α/β-SNAP (77.1) and SNAP-25 (71.2) were provided by R. Jahn and S. Engers (Gottingen, Germany). Rabbit polyclonal antibodies directed against syt II were kindly provided by M. Fukuda (Ibaraki, Japan) (Fukuda and Mikoshiba, 2000). Anti-BoNT/A, B and E antibodies were generated by immunizing rabbits with formalin treated purified neurotoxin; antibodies were affinity purified using immobilized neurotoxin.

cDNA and Recombinant Proteins— cDNA encoding rat syt I (Perin et al., 1990), mouse syt II and IX (Fukuda and Mikoshiba, 2000), and rat syt IV (Vician et al., 1995) were provided by T. C. Sudhof (Dallas, Tex.), M. Fukuda (Ibaraki, Japan) and H. Herschman (Los Angeles, Calif.), respectively. Full length syb II was generated as a GST-fusion protein as described (Lewis et al., 2001) using a cDNA provide by R. Scheller (Stanford, Calif.).

To screen for toxin binding activity, we generated truncated versions of syt I, II, IV and IX that lacked the C2B-domain but contained all other domains. A number of additional constructs (truncations and chimeras, as indicated in the figures) were also generated by PCR, subcloned into pGEX-2T and expressed and purified as described (Chapman et al., 1996; Lewis et al., 2001). Syt II 1-267 and 61-267 were also subcloned into pTrcHis and purified as N-terminal tagged His6 fusion proteins as described (Chapman et al., 1996).

Pull-Down Assays—

Recombinant proteins were immobilized as GST fusion proteins bound to glutathione-Sepharose beads. Unless otherwise indicated, 10 µg of immobilized protein was mixed with the indicated concentrations of BoNT/B, A or E either with (+; 25 µg/ml) or without (−) gangliosides in 100 µl of Tris buffered saline (TBS; 20 mM Tris, 150 mM NaCl, pH 7.4) plus 0.5% Triton X-100 for 1 hour at 4° C. Beads were washed three times, bound proteins were solubilized by boiling in SDS-sample buffer and subjected to SDS-PAGE and visualized by staining with Coomassie Blue or by immunoblot analysis using anti-toxin antibodies. In all blots, the immunoreactivity for the toxin heavy chain is shown.

A peptide corresponding to residues 40-60 of mouse syt II, P21, and a scrambled version of this peptide, P21S (IK-MNDAEFFGKSNFQEKLEKEC, SEQ ID NO:5), were synthesized (Biotech Center, UW-Madison) with an added C-terminal cys which was used to conjugate them to agarose beads (at 1 mg/ml) using a Sulfolink Kit (Pierce). Fifty µl of the conjugated agarose gel was used in the pull down assays.

PC12 Cell Lines and Immunoblot Analysis—

PC12 cells were cultured as described (Klenchin et al., 1998). To generate cells that express syt II (syt II$^+$), full length mouse syt II was subcloned into pcDNA3.1(−) (ClonTech) and transfected into PC12 cells via electroporation. Transfected cells were selected with G418 (1 mg/ml) and several independent monoclonal cell lines were established. Cells were harvested in PBS plus 0.5% Triton X-100, 0.05% SDS and 5 mM PMSF, and incubated for 30 min at 4° C. on a shaker. Samples were centrifuged at 21,000×g for 10 min, and the concentration of protein in the supernatant was determined using BCA (Pierce). Samples were subjected to SDS-PAGE and immunoblot analysis; blots were developed using enhanced chemiluminescence (ECL) (Pierce).

Entry of BoNTs into PC12 Cells—

In experiments that did not involve pre-loading, cells were grown to 70% confluence and incubated with BoNT for 48 hrs. For experiment in which cells were pre-loaded with gangliosides, cells were grown to 80% confluence followed by incubation in serum-free media plus 250 µg/ml gangliosides. Twenty four hrs later, the serum-free/ganglioside media was replaced with complete media and the cells were incubated with toxin for 48 hrs. Cells were harvested and entry of CNTs was assayed via immunoblot analysis using antibodies directed against syb II or SNAP-25.

Figure 5:
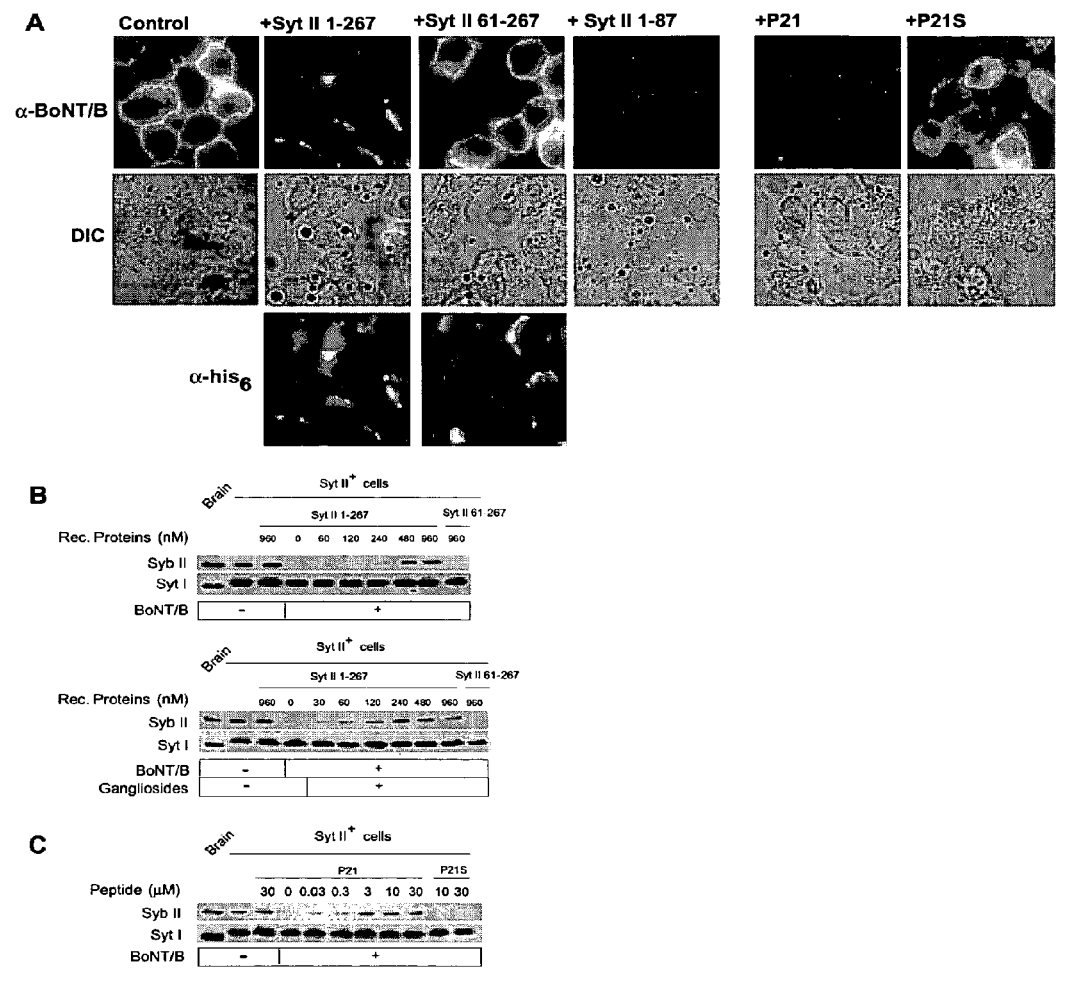

For blocking experiments, syt II 1-267 and syt 61-267 were generated as his6-fusion proteins; syt II 1-87 was generated as a GST-fusion protein that was eluted from beads using 10 mM glutathione plus 0.5% Triton X-100. Protein fragments or peptides were pre-mixed with BoNT/B in 200 µl TBS for 1 hr at 4° C. before adding into 2 ml of cell culture media (per well in a 6 well plate). In some cases, gangliosides were also added in the binding buffer (FIG. 5 B, lower panel). The final concentration of BoNT/B was 30 nM, the final concentration of gangliosides was 25 µg/ml, and the final [syt fragment] is indicated in the description of the drawings.

Binding of BoNT/B to PC12 Cells—

Cells treated with toxin, plus or minus pre-incubation with syt fragments, were washed three times with PBS, fixed with 4% paraformaldehyde (15 min at room temperature), permeabilized with 0.1% Triton X-100 (10 min at room temperature), and stained with a rabbit anti-BoNT/B primary antibody and an FITC conjugated goat anti-rabbit secondary antibody (Jackson Laboratories). In the syt II fragment competition assays described in FIG. 5, syt II 1-267 and 61-267 fragments form aggregates bound to cells (Bai et al., 2000)—these were visualized using a mouse anti-his6 primary antibody (Qiagen) and a Rhodamine-conjugated goat anti-mouse secondary antibody (Jackson Laboratories). The fluorescence images were obtained as described for the motor nerve terminal experiments. We note that for these experiments free detergent was removed from the recombinant syt fragments by washing the immobilized proteins with detergent-free buffers prior to elution. However, in the case of syt II 1-87, low levels of Triton X-100 were needed to elute the protein from the beads; because of this, experiments using this fragment were carried out within 6 hrs to avoid effects of detergent on the cells.

Antibody and Toxin Uptake Experiments—

Cells were treated with either control solution (15 mM HEPES, 145 mM NaCl, 5.6 mM KCl, 2.2 mM $CaCl_2$, 0.5 mM $MgCl_2$, 5.6 mM glucose, 0.5 mM ascorbic acid, 0.1% BSA, [pH 7.4]), or high [$K^+$] solution (same as control solution but adjusted to 95 mM NaCl and 56 mM KCl), for 10 min at 37° C., in the presence of BoNT/B plus 10 µl monoclonal antibody against the luminal ($\alpha$-syt $I_N$; clone 604.4) or cytoplasmic domain of syt I ($\alpha$-syt $1_c$; clone 41.1). Cells were washed with culture media, incubated for 30 min 37° C., fixed and permeabilized. A rabbit anti-BoNT/B primary antibody was used to stain BoNT/B; staining was visualized using an FITC conjugated goat anti-rabbit secondary antibody. Rhodamine conjugated goat anti-mouse secondary antibodies were used to visualize internalized syt I antibodies. Confocal images were collected with a Bio-Rad MRC 1000 confocal microscope (Keck Center for Biological Imaging, UW-Madison) using a 100× oil-immersion objective.

Co-Immunoprecipitation—

Recombinant syt I 1-265 GST was purified as described above and cleaved from the GST tag using thrombin. Five µl of monoclonal antibody $\alpha$-syt $I_N$ (604.4) was incubated with BoNT/B (300 nM), with or without 1.5 µM Syt I 1-265, in 100 µl TBS plus 0.5% Triton X-100 and gangliosides (25 µg/ml), for 1 hr at 4° C. Thirty µl Protein G fast flow beads (Pharmacia) was added, samples were mixed for 1 hr, beads were washed three times in binding buffer, and bound material was analyzed by SDS-PAGE and immunoblotting using an anti-BoNT/B polyclonal antibody and $\alpha$-syt $I_N$ (604.4).

Rat Hemi-Diaphragm Experiments—

Rats hemi-diaphragms were placed in ice-cold ringer (in mM: NaCl 138.8, KCl 4, $NaHCO_3$ 12, $KH_2PO_4$ 1, $MgCl_2$ 2, $CaCl_2$ 2, glucose 11) gassed with 95% $CO_2$/5% $O_2$. Stimulation was carried out with a similar solution where KCl was increased to 45 mM, and the NaCl appropriately reduced. Hemi-diaphragms were incubated with high potassium ringer containing 5 nM BoNT/B for 10 min at room temperature. In some experiments the BoNT/B was pre-mixed with either the syt II fragment 1-267, or fragment 61-267, both mixed with 25 µg/ml gangliosides. At the end of the stimulation/incubation period, the preparations were fixed (4% paraformaldehyde), permeabilized (0.3% Triton X-100), and blocked in goat serum prior to immunolabeling with a rabbit anti-BoNT/B antibody and a monoclonal anti-Syb II antibody Immunofluorescence was visualized using a FITC-conjugated anti-rabbit antibody, and a TRITC-conjugated anti-mouse antibody. A region of muscle adjacent to the site of nerve entry (where a large number of surface nerve terminals are to be found) was placed in a viewing chamber with a glass bottom comprising a single cover slip Immunofluorescence images were obtained using a Nikon TE300 microscope, with a microMAX cooled CCD camera controlled by MetaMorph software. Fluorescence intensities were quantified using ImageJ software.

Neutralization of BoNT/B Activity In Vivo—

For each batch of BoNT/B, the $LD_{50}$ value for mice (20-22 g; Institute of Cancer Research strain) was determined using standard methods (Schantz and Kautter, 1978). The $LD_{50}$ corresponds to the amount of toxin, introduced via intra peritoneal injection, that results in 50% death after 4 days. Our preparations of BoNT/B had activities of about $10^8$ $LD_{50}$/mg. For toxin neutralization studies, we made use of the more rapid intravenous time-to-death assay (Boroff and Fleck, 1966). We first generated a standard curve in which the relationship between time-to-death of mice injected, intravenously, with 100 µl BoNT/B (expressed in min) is plotted versus the specific toxicity of BoNT/B that was determined using the standard method described above (log [$LD_{50}$/ml]). Within the linear range, $10^4$-$10^6$ $LD_{50}$/ml, this plot was used to convert experimentally determined time-to-death, from intravenous injection of relatively large doses of toxin, to $LD_{50}$/ml values. For the toxin neutralization experiments, BoNT/B was premixed with gangliosides alone (250 µg/ml) or gangliosides plus the indicated syt II fragments for 10 min at room temperature and then injected intravenously into mice. In all experiments, the total injection volume was always 100 µl. Neutralization of the toxin is indicated by an extension in the time-to-death of mice injected with toxin alone versus injection with toxin that had been pre-mixed with syt fragments/gangliosides. The increase in the time-to-death was converted into a decrease in the apparent [$LD_{50}$/ml] using the standard curve, and the percentage of neutralization was calculated using the expression: 1−[$LD_{50}$/ml(+syt II fragment)/$LD_{50}$/ml (−syt II fragment)]×100, where (+syt II fragment) refers to samples that contain toxin, gangliosides and recombinant proteins and (−syt II fragment) samples were composed of toxin and gangliosides only.

Results

A Region within the Luminal Domain of Syt I and II Mediates Direct Interactions with BoNT/B—

To assay for direct syt.BoNT interactions, fragments of syt I and II were immobilized as GST fusion proteins and used as an affinity matrix to pull down BoNT/A, B or E in the presence and absence of gangliosides. For these experiments, we included two other syt isoforms, syt IV and IX, as well as full length syb II, as negative controls. The structure of the syt fragments are shown in FIG. 1A (upper panel). Because each fragment contains a transmembrane domain, binding assays included 0.5% Triton X-100; thus, gangliosides were presented as mixed micelles. In contrast to a previous study (Li and Singh, 1998), we did not observe detectable binding of BoNT/A or E to any of the immobilized proteins (FIG. 1A, middle panel), even when relatively high concentrations of BoNT/A and E were employed (300 nM; data not shown), indicating that these toxins do not bind to the syt fragments used in our assays.

Under identical conditions, we observed that BoNT/B binds syt I and II. While syt I.BoNT/B interactions were strictly dependent on gangliosides, syt II bound BoNT/B in the absence of gangliosides (FIG. 1A, middle panel). Reducing the concentration of bead-immobilized GST-syt II fusion protein revealed that gangliosides can enhance syt II.BoNT/B interactions (FIG. 1A, lower panel), but this interaction is clearly less dependent on gangliosides. These findings are consistent with previous data showing that syt II binds BoNT/B more tightly than does syt I (Nishiki et al., 1996a); presumably, the higher affinity syt II.BoNT/B interaction is less reliant on gangliosides. Syt I/II.BoNT/B interactions are specific, since binding to an analogous region of syt IV or IX, or to full length syb II, was not detected (FIG. 1A, middle panel).

If syt I and II are physiologically relevant receptors for BoNT/B, binding must be mediated by the region of syt that is exposed outside of cells—i.e. the luminal domain—during cycles of exocytosis and endocytosis. To clarify how BoNT/B binds to syt II, we first used syt II/IX chimeras. Swapping the luminal domains of these proteins was sufficient to transfer the BoNT/B binding activity from syt II to syt IX (FIG. 1B), indicating that BoNT/B binding is mediated by the luminal domain of syt II. Consistent with this finding, a shorter fragment of syt II, composed of only the luminal and transmembrane domain (residues 1-87), mediated stoichiometric binding of the toxin (FIG. 1C).

Figure 2:
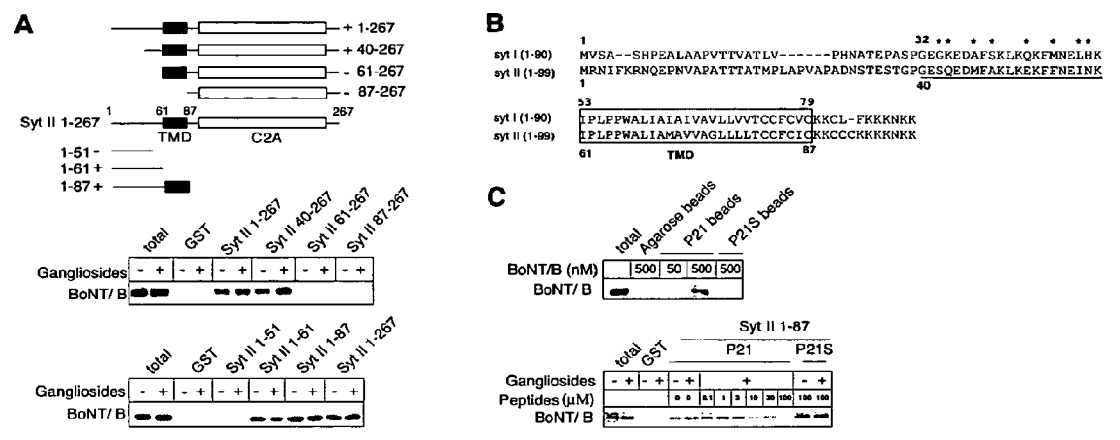
Figure 8:
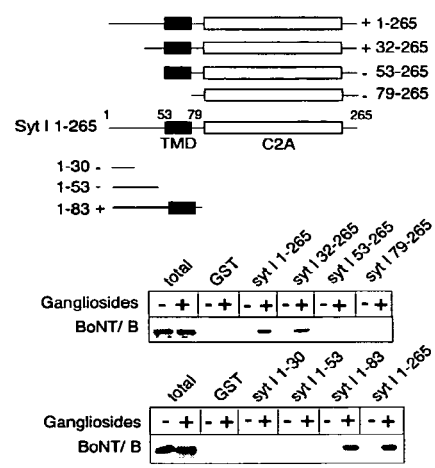
FIG. 8 shows the mapping the BoNT/B binding site within the luminal domain of syt I. Binding assays were carried out as described in FIG. 2A, using the indicated syt I truncation mutants. The upper panel shows a schematic of the truncation mutants where (+) denotes binding and (−) denotes lack of binding.

Truncation analysis was used to further map the toxin binding site of syts I and II. Within the luminal domain of syt II, residues 40-60, which are adjacent to the transmembrane domain, are critical for toxin binding (FIG. 2A). We note that fragment 61-267 of syt II can bind gangliosides via its transmembrane domain (residues 61-87) (Kozaki et al., 1998), yet this fragment fails to bind BoNT/B in the presence of gangliosides (FIG. 2A, middle panel). These data suggest that gangliosides do not directly mediate toxin binding under our assay conditions, but rather cooperate with the luminal domain to form high affinity BoNT/B binding sites. The analogous membrane proximal region of syt I (residues 32-52) was also critical for binding of BoNT/B (FIG. 8). This segment is highly conserved between syt I and II (FIG. 2B); minor sequence differences may account for the differences in affinity for BoNT/B (Nishiki et al., 1996a). We note that the isolated luminal domain of syt II (residues 1-61) but not syt I (residues 1-53), bound to BoNT/B (FIG. 2A and FIG. 8). This result is likely due to the strong ganglioside requirements for syt I.BoNT/B interactions; deletion of the transmembrane domain of syt I abolishes ganglioside binding (Kozaki et al., 1998) and thereby decreases BoNT/B binding activity.

The mapping studies described above suggest that residues 40-60 of syt II comprise the BoNT/B binding domain. To test this directly, a synthetic peptide (P21) corresponding to this segment of syt II was immobilized on beads and used as an affinity matrix. This peptide binds directly to BoNT/B, although less avidly than do longer fragments of syt II since detectable binding required higher concentrations of the toxin (FIG. 2C, upper panel). A scrambled version of this peptide, P21S, served as the negative control. Furthermore, P21, but not P21S, was able to competitively inhibit syt II.BoNT/B interactions (FIG. 2C, lower panel). P21 also inhibited syt I.BoNT/B interactions (data not shown). Together, these studies establish that residues 40-60 of syt II largely mediate binding of BoNT/B.

Syt I Mediates Ganglioside Dependent Binding and Entry of BoNT/B into PC12 Cells—

Figure 3:
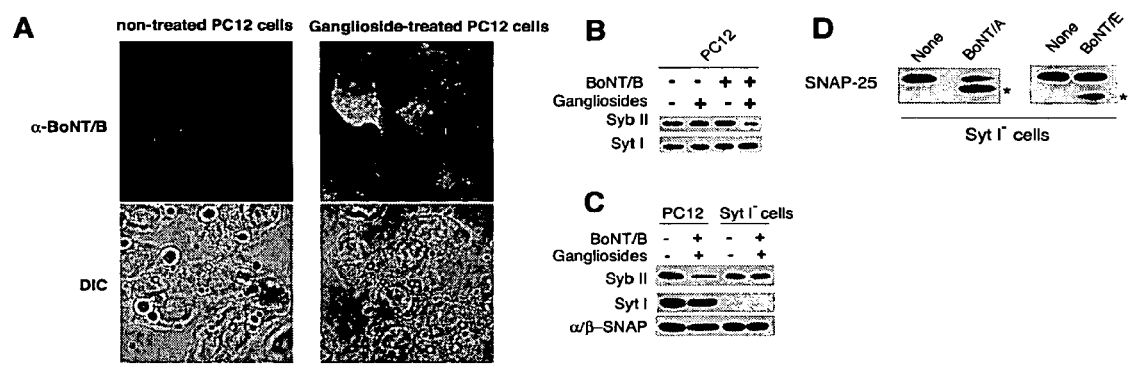
FIG. 3 shows that entry of BoNT/B into PC12 cells is dependent on syt I expression and pre-loading of cells with gangliosides. A) PC12 cells were either untreated or pre-loaded with gangliosides. Cells were then incubated with 50 nM BoNT/B for 48 hr, fixed with 4% paraformaldehyde, permeabilized with 0.1% Triton X-100, and stained using a rabbit anti-BoNT/B antibody; the secondary antibody was goat anti-rabbit-FITC. Pre-loading cells with gangliosides resulted in toxin binding activity. B) PC12 cells either were (+) or were not (−) preloaded with gangliosides; cells were then incubated with (+) or without (−) 50 nM BoNT/B for 48 hr and harvested. Twenty µg of each sample was subjected to SDS-PAGE and immunoblot analysis using anti-syb II (Cl 69.1) or anti-syt I (Cl 41.1) antibodies. Pre-loading cells with gangliosides mediated entry of toxin, as evidenced by cleavage of syb II. Syt I was probed to ensure equal loading on the gels. C) Experiments were carried out as in (B) above, except that wild type PC12 cells were compared to the syt I⁻ cells (Shoji-Kasai et al., 1992). α/β-SNAP was probed to ensure equal loading. In the absence of syt I, BoNT/B cannot enter PC12 cells to cleave syb II, even when cells have been preloaded with gangliosides. D) Entry of BoNT/A and E into Syt I⁻ PC12 cells. Syt I⁻ PC12 cells were incubated with 30 nM BoNT/A or 50 nM BoNT/E for 48 hrs; entry was monitored by assaying for cleavage of SNAP-25. Asterisks denote SNAP-25 cleavage products.

The experiments described above demonstrate that syt I and II bind to BoNT/B through a conserved region in their ecto-domains. The key question, however, is whether syt I or II mediate entry of the toxin; namely, are they functional protein receptors for BoNT/B? To address this question we first used PC12 cells, a neuroendocrine cell line that serves as a model system to study $Ca^{2+}$ triggered exocytosis. These cells express the substrates for all of the CNTs but are resistant to entry of BoNT/B, probably due to lack of functional toxin receptors (Lomneth et al., 1991). PC12 cells express syts I and IX and trace levels of syt IV; other syt isoforms are not expressed at significant levels (Zhang et al., 2002). Since syt IX and IV do not bind BoNT/B and syt I binds only in the presence of gangliosides (FIG. 1A, middle panel), toxin resistance could be due to the fact that these cells contain low levels of gangliosides as compared to neurons (Walton et al., 1988). We tested this idea by pre-loading exogenous gangliosides into the plasma membrane of wild type PC12 cells. As shown in FIG. 3A, detectable toxin binding was observed only when cells were loaded with gangliosides. We then determined whether the toxin can enter ganglioside-treated cells. To monitor entry we assayed for cleavage of the cytoplasmic substrate of BoNT/B, syb II (Schiavo et al., 1992) by immunoblot analysis using anti-syb II antibodies. Cleavage of syb II by BoNT/B occurred only when cells were first pre-loaded with gangliosides (FIG. 3B). These data are consistent with a model in which syt I and gangliosides cooperate to mediate the binding and entry of BoNT/B, and are in agreement with biochemical data showing that the toxin binds to syt I only in the presence of gangliosides. To further test this model, we took advantage of a PC12 cell line that lacks syt I (Syt I−) (Shoji-Kasai et al., 1992). This cell line is still capable of $Ca^{2+}$-triggered exocytosis, presumably via the redundant action of syt IX (Fukuda et al., 2001; Zhang et al., 2002). As shown in FIG. 3C, BoNT/B failed to cleave syb II in ganglioside-loaded syt I− PC12 cells. These data indicate that gangliosides plus syt I are both needed for toxin entry.

We also assayed for entry of BoNT/A and E into PC12 cells. Entry was monitored by assaying for cleavage of their substrate SNAP-25 (Blasi et al., 1993a; Schiavo et al., 1993). BoNT/A cleaves SNAP-25 between residues 197-198, thereby removing 9 amino acids; BoNT/E cleaves between residues 180-181 and removes 26 residues (Schiavo et al., 1993). Incubation of cells with nM concentrations of BoNT/A and E resulted in similar degrees of cleavage of SNAP-25 in both wild type (data not shown) and syt I− cells (FIG. 3D). Thus, both toxins are able to enter syt I− PC12 cells that have not been pre-loaded with gangliosides. These experiments demonstrate that syt I/II are not required for entry of BoNT/A and E into PC12 cells, and that syt I− cells are competent to take-up at least some CNTs.

Syt II is Sufficient to Mediate Entry of BoNT/B into PC12 Cells—

Figure 4:
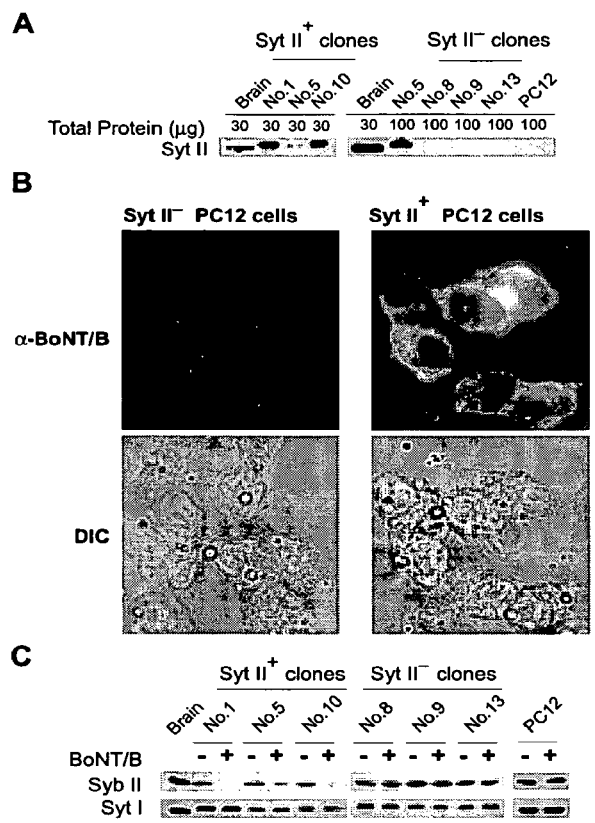
FIG. 4 shows that Syt II mediates entry of BoNT/B into PC12 cells. A) Full length mouse syt II was subcloned into pcDNA3.1(−) and used to transfect PC12 cells. Cells were selected with G418 and several independent monoclonal lines were established and screened for syt II expression by immunoblot analysis using a rabbit anti-syt II antibody; 30 µg of protein from the syt II⁺ clones and 100 µg from the syt II⁻ clones were loaded onto the gels. Clone No. 1, 5 and 10 expressed syt II (syt II⁺), clone No. 8, 9 and 13 lacked syt II (syt II⁻). Since clone No. 5 expressed low levels of syt II (left panel), a 100 µg sample from this clone was also included in the blots of the syt II⁻ clones to confirm that this clone expresses syt II. B) Wt or syt II⁺ (clone No. 1) PC12 cells were decorated with 30 nM BoNT/B as described in FIG. 3A. C) Entry of BoNT/B (15 nM) into PC12 cells was assayed as described in FIG. 3B. Entry of the toxin was observed in all syt II⁺ clones, and was not observed in any of the syt II⁺ clones. As a control, a parental PC12 cell line was analyzed in parallel.

To determine directly whether syt II can function as a receptor for BoNT/B, we took advantage of the observation that this syt isoform is able to bind BoNT/B to some extent in the absence of gangliosides (FIG. 1A). We generated PC12 cell lines that stably express syt II (Syt II+; FIG. 4A) and observed that they bind BoNT/B without preloading cells with exogenous gangliosides (FIG. 4B). A key finding was that expression of syt II was sufficient to reconstitute toxin entry into the transfected cells, as shown by the cleavage of syb II (FIG. 4C). The efficiency of cleavage was proportional to the level of syt II expression, and cleavage was not observed in cells lacking syt II (FIG. 4C, right panel). These findings demonstrate that syt II can function as a receptor for BoNT/B without pre-loading cells with exogenous gangliosides.

To further test whether binding and entry is mediated by direct interactions between BoNT/B and the luminal domain of syt II, we determined whether fragments of syt II that contain the BoNT/B binding site inhibit toxin action. As shown in FIG. 5A, fragments corresponding to residues 1-267, 1-87 and 40-60 (P21) of syt II, blocked binding of BoNT/B to syt II+ PC12 cells. Syt II fragment 61-267, which lacks the luminal domain, and the scrambled peptide P21S, failed to block binding of the toxin. We note that syt II 1-267 and 61-267 contain an oligomerization domain within residues 61-140, and also bind membranes via their C2A-domain, thus forming aggregates (Bai et al., 2000). These aggregates are visualized in FIG. 5A (bottom panels) using an anti-his6 antibody that recognizes a his6-tag present in these recombinant syt fragments. The syt 1-267 fragment also contains bound BoNT/B, as shown via the anti-BoNT/B immunoreactivity in the syt II aggregates (FIG. 5A, upper panel). In contrast, cell-associated syt II 61-267 aggregates did not contain BoNT/B (FIG. 5A, lower panel).

More importantly, titration of syt II 1-267 resulted in the dose-dependent protection of syb II cleavage; fragment 61-267 had no protective effect (FIG. 5B, upper panel). Inclusion of gangliosides increased the efficacy of protection by about 3-fold (FIG. 5B, lower panel), presumably by facilitating the already robust binding of syt II 1-267 to BoNT/B (FIG. 1A, lower panel). This result is consistent with the observation that the binding partner with the highest affinity for BoNT/B is composed of syt II plus gangliosides (FIG. 1A, lower panel; (Nishiki et al., 1996a)). As a control, mixtures of gangliosides and syt II fragment 61-267 were not able to prevent cleavage of syb II (FIG. 5B, lower panel). P21 also yielded dose-dependent protection, albeit at >10-fold higher concentrations as compared to the 1-267 fragment (FIG. 5C), presumably because it binds less tightly to BoNT/B than the longer fragments of syt II. There is a concern that low levels of detergent associated with the transmembrane domains present in some of the syt fragments may affect the uptake and action of the toxin. However, we did not observe any apparent toxicity using these fragments. Also, the ability of fragment 1-267 to block the action of the toxin cannot be due to toxicity from associated detergent, as fragment 61-267 has the same transmembrane domain yet fails to provide any protection.

Activity Dependent Entry of BoNT/B into Vesicles that Contain Syt I—

Figure 9:
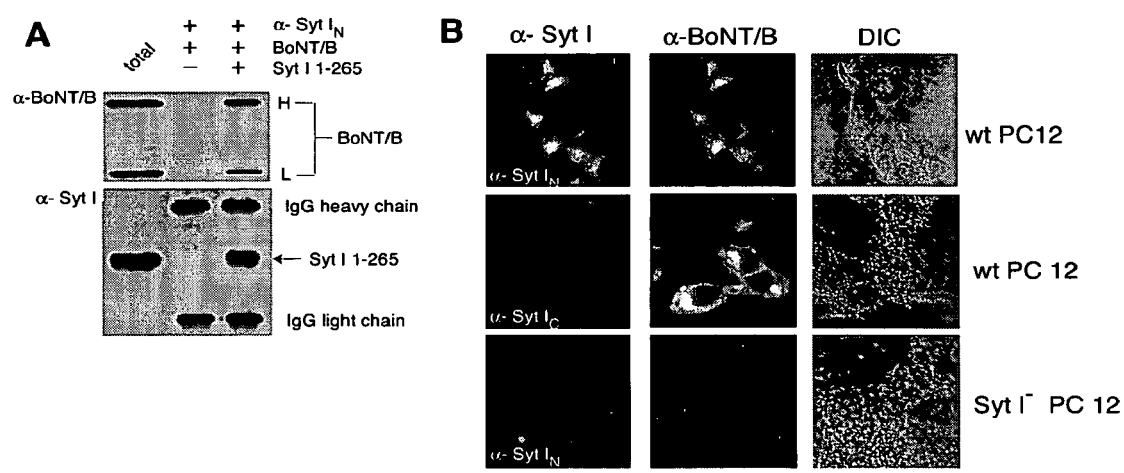
FIG. 9 demonstrates the simultaneous and specific internalization of syt I luminal domain antibodies and BoNT/B into PC12 cells. A) BoNT/B and α-syt $I_N$ antibodies simultaneously bind to syt I. Co-immunoprecipitation of the syt I 1-265 fragment (1.5 μM) with BoNT/B (300 nM) was carried out as described in Methods Immunoprecipitated toxin and syt I 1-265 were detected on western blots using ECL. B) PC12 cells were pre-loaded with gangliosides and incubated with BoNT/B (50 nM) plus α-syt $I_N$ (10 μl/ml) antibodies for 10 min at 37° C. in high [K$^+$] buffers. Cells were then washed, fixed and permeabilized as described in Methods section of the Example below. Top panel: PC12 cells were able to take up α-syt $I_N$ antibodies and BoNT/B after depolarization. Middle panel: Experiments were carried out as above, except the α-syt $I_C$ antibodies were used—this antibody was not taken up following depolarization, and thus serves as a negative control. Bottom panel: Experiments were carried out as described in panel (A) above, except that syt I$^-$ cells were used. Syt I$^-$ cells were unable to take up either the α-syt $I_N$ antibody or BoNT/B.

The data above suggest a model in which BoNT/B gains entry into PC12 cells by binding to the luminal domain of syt I or II. This model predicts that BoNT/B will follow the internalization of syt I/II from the cell surface into the same organelles and that internalization should be activity-dependent. The exocytosis/endocytosis of vesicles can be tracked using antibodies directed against the N-terminal luminal domain of syt I (Juzans et al., 1996; Mateeoli et al., 1992). First, we demonstrated that an anti-syt I luminal domain antibody ($\alpha$-syt $I_N$) and BoNT/B can bind to syt I simultaneously (FIG. 9A). This is the expected result, since the antibody recognizes the first twelve amino acids at the N-terminus of syt I, while the BoNT/B binding site lies at the C-terminal end of the luminal domain.

We took advantage of this finding and determined whether the antibody and toxin are taken-up into the same compartment in response to stimulation. PC12 cells were pre-loaded with gangliosides and depolarized with high [K+] to induce exocytosis of secretory vesicles in the presence of $\alpha$-syt $I_N$ antibodies and BoNT/B. Exocytosis and endocytosis were allowed to proceed for 10 minutes, followed by extensive washes to remove surface-bound antibody and toxin. Both $\alpha$-syt $I_N$ antibodies and BoNT/B were observed to be internalized into the same compartment. Depolarization of cells significantly increased the internalization of both the antibody and BoNT/B; only low levels of internalization, due to spontaneous exocytosis and recycling, were observed in the control.

In contrast to the $\alpha$-syt $I_N$ antibody, an antibody directed against the cytoplasmic domain of syt I ($\alpha$-syt $I_C$) was not taken-up (FIG. 9B), demonstrating that staining with the luminal domain antibody is not due to loss of integrity of the cell membranes. Also, $\alpha$-syt $I_N$ antibodies and BoNT/B were not taken-up into syt $I^-$ PC12 cells (FIG. 9B), further establishing that uptake requires the exposure of the syt I luminal domain and is not due to bulk endocytosis. These findings demonstrate that the luminal domain of syt I is exposed on the surface of PC12 cells during exocytosis, and that BoNT/B enters PC12 cells via organelles that contain syt I. This latter observation was further confirmed by the co-localization of BoNT/B with an antibody directed against the cytoplasmic domain ($\alpha$-syt $I_C$) of syt I.

Similar results were obtained using syt $II^+$ PC12 cells—BoNT/B entered syt I containing vesicles in an activity dependent manner (data not shown). We have been unable to localize syt II in the syt $II^+$ cell lines using currently available antibodies. However, syt II is co-localized with syt I on secretory vesicles in brain and is likely to be targeted to syt I containing organelles in PC12 cells (Osborne et al., 1999).

Activity Dependent Uptake of BoNT/B into Motor Nerve Terminals—

Figure 6:
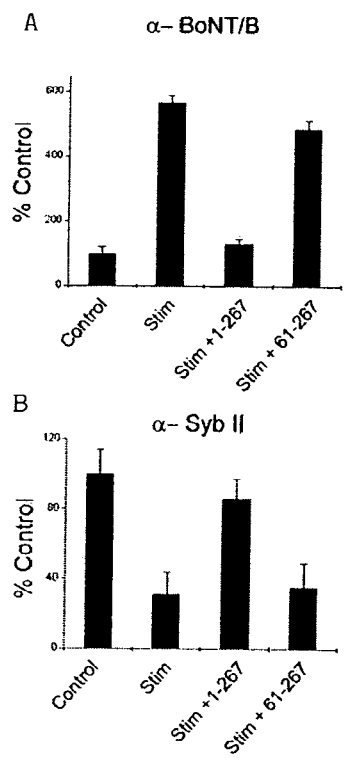
FIG. 6 shows activity dependent uptake of BoNT/B, followed by cleavage of syb II in rat diaphragm motor nerve terminals. Rat diaphragm preparations were incubated with BoNT/B (5 nM) in mammalian ringer. They were either unstimulated (control), stimulated with high potassium (stimulated), or stimulated in the presence of a mixture of BoNT/B and the protein fragment syt II 1-267 or 61-267 (1 µM) plus gangliosides (25 µg/ml). They were then fixed, permeabilized and blocked. Control (unstimulated) nerve terminals show bright immunofluorescence for syb II, and very dim labeling of BoNT/B. Stimulation during incubation with BoNT/B resulted in greatly reduced syb II immunofluorescence, while BoNT/B levels are markedly enhanced. Stimulation in the presence of both BoNT/B and syt II 1-267/gangliosides resulted in protection of nerve terminals, seen as both preservation of syb II staining, and greatly reduced levels of BoNT/B binding. A) Quantification of BoNT/B levels under different conditions. Stimulation greatly enhances BoNT/B binding, and this can be blocked by co-incubation with syt II 1-267/gangliosides. Syt fragment 61-267 plus gangliosides failed to block binding of BoNT/B. B) Quantification of syb II levels. Syb II levels show a complementary pattern to those seen with BoNT/B. Levels of immunofluorescence are high in unstimulated tissue, but drop after stimulation. Inclusion of syt II 1-267/gangliosides but not 61-267/gangliosides with BoNT/B protects syb II from cleavage. In panels (A) and (B), error bars represent the standard error of the mean (N=15-22).

The cause of death from BoNT/B intoxication is asphyxiation due to blockade of neurotransmission at the diaphragm. We therefore extended our studies to explore the mechanism of toxin entry into neurons in this tissue. Only low levels of association of BoNT/B with motor nerve terminals in the rat diaphragm were observed under resting conditions. However, stimulation with KCl results in a dramatic increase in the levels of BoNT/B (5.7-fold; FIG. 6A), and a concomitant loss of syb II immunoreactivity (3.2-fold; FIG. 6B). The increase in binding of BoNT/B and the loss of syb II were virtually abolished by incubation with the syt II fragment 1-267/gangliosides, but not by a mixture of syt II 61-267/gangliosides (FIGS. 6A,B). These data demonstrate that uptake of BoNT/B is activity dependent at its natural target. Moreover, binding and entry of the toxin can be prevented by syt II fragments that contain the toxin binding site while syt fragments lacking the toxin binding site have no effect.

Competitive Inhibition of Syt.BoNT/B Interactions Neutralizes BoNT/B In Vivo—

Figure 7:
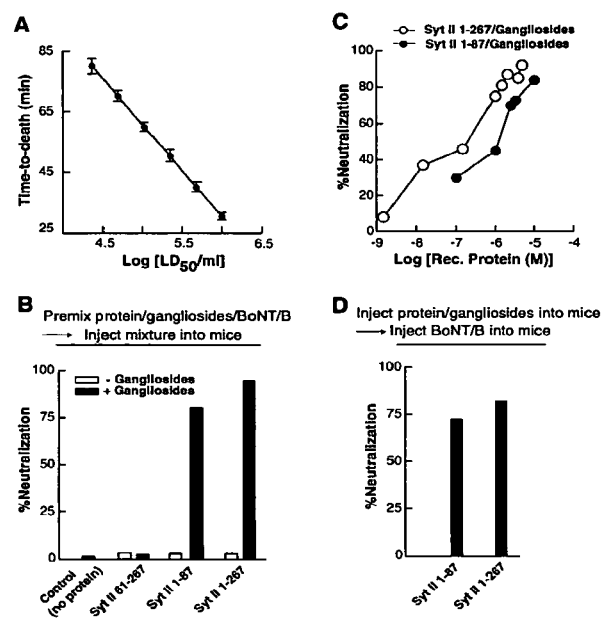

The experiments described above demonstrate that BoNT/B enters PC12 cells and motor nerve terminals through interactions with syt I/II plus gangliosides. To further establish the physiological relevance of the above findings, we determined whether syt II fragments that contain the BoNT/B binding site can neutralize the effects of the toxin in vivo. For these studies, we used a rapid method to evaluate toxicity in which the intravenous injection of large amounts ($10^5$-$10^6$ $LD_{50}$) of BoNT/B into mice result in death on a time scale of minutes to hours, as opposed to standard four day lethality assays (in which 1 $LD_{50}$ is defined as the amount of toxin that results in 50% death after four days) (Boroff and Fleck, 1966; Schantz and Kautter, 1978). This assay reduces the amount of time that animals are exposed to the toxin. To this end, we first established a standard curve to relate classically determined $LD_{50}$/ml values to the time-to-death values that were determined using the rapid assay (FIG. 7A). This plot was then used to convert the experimentally measured time-to-death to units of apparent $LD_{50}$/ml. After this conversion, the apparent $LD_{50}$/ml values were used to calculate the % neutralization of the toxin by syt/ganglioside mixtures.

The range of [syt II 1-267] that we tested in mice did not afford substantial protection in the absence of gangliosides. Syt II fragments 1-267 and 1-87, together with gangliosides, neutralized most of the BoNT/B toxicity in mice (FIG. 7B). We believe that in order for syt II 1-267 itself to provide protection in vivo, higher doses are required.

Syt II 61-267 plus gangliosides did not neutralize the toxin (FIG. 7B), further establishing the essential role of the luminal domain of syt II for toxin entry in vivo. The potencies of syt II 1-267 and 1-87 were determined (FIG. 7C); both fragments yielded dose-dependent protection at sub-$\mu$M concentrations. Finally, prior intravenous injection with syt II 1-267 or 1-87, mixed with gangliosides, neutralized 70-80% of BoNT/B that was injected 1 minute later (FIG. 7D), indicating that animals can be protected prior to exposure to toxin.

The present invention is not intended to be limited to the foregoing examples, but rather to encompass all such variations and modifications as come within the scope of the appended claims.

REFERENCES (All of which are Herein Incorporated by Reference in their Entirety)

1. Amon et al. 2001. Jama. 285:1059-70.
2. Bai et al. 2000. J Biol. Chem. 275:25427-35.
3. Blasi et al. 1993a. Nature. 365:160-3.
4. Blasi et al. Embo J. 12:4821-8.
5. Boroff et al. 1966. J. Bacteriol. 92:1580-1.
6. Bullens et al. 2002. J. Neurosci. 22:6876-84.
7. Chapman, E. R. 2002. Nat Rev Mol Cell Biol. 3:498-508.
8. Chapman et al. 1996. J Biol. Chem. 271:5844-9.
9. Dasgupta et al. 1970. Biochim Biophys Acta. 214:343-9.
10. Dolly et al. 1984. Nature. 307:457-60.
11. Evans et al. 1986. Eur J. Biochem. 154:409-16.
12. Fukuda et al. 2001. J Biol. Chem.
13. Fukuda et al. 2000. J Biol. Chem. 275:28180-5.
14. Halpern et al. 1995. Curr Top Microbiol Immunol. 195: 221-41.
15. Hatheway, C. L. 1995. Curr Top Microbiol Immunol. 195:55-75.
16. Herreros et al. 2001. Mol Biol Cell. 12:2947-60.
17. Jahn et al. 1994. Ann N Y Acad. Sci. 733:245-55.
18. Juzans et al. 1996. Pflugers Arch. 431:R283-4.
19. Kerner, J. 1817. Tübinger Blatter. 3:1-25.
20. Kitamura et al. 1999. Biochim Biophys Acta. 1441:1-3.
21. Kozaki et al. 1998. Microb Pathog. 25:91-9.
22. Lewis et al. 2001. J Biol. Chem. 276:15458-65.
23. Li et al. 1998. J Nat. Toxins. 7:215-26.
24. Lomneth et al. 1991. J. Neurochem. 57:1413-21.
25. Mahant et al. 2000. J Clin Neurosci. 7:389-94.
26. Matteoli et al. 1992. J. Cell Biol. 117:849-61.
27. Montecucco, C. 1986. TIBS:314-317.
28. Nishiki et al. 1994. J Biol. Chem. 269:10498-503.
29. Nishiki et al. 1996a. FEBS Lett. 378:253-7.
30. Nishiki et al. 1996b. Neurosci Lett. 208:105-8.
31. Osborne et al. 1999. J Biol. Chem. 274:59-66.
32. Perin et al. 1990. Nature. 345:260-3.
33. Schantz et al. 1978. J. Assoc. Off. Anal. Chem. 61:96-99.
34. Schengrund et al. 1996. J. Neurochem. 66:2556-61.
35. Schengrund et al. 1993. Neurosci Lett. 158:159-62.
36. Schengrund et al. 1992. Brain Res Bull. 29:917-24.
37. Schiavo et al. 1992. Nature. 359:832-5.
38. Schiavo et al. 2000. Physiol Rev. 80:717-66.
39. Schiavo et al. 1998. Biochem Biophys Res Commun. 248:1-8.
40. Schiavo et al. 1993. FEBS Lett. 335:99-103.
41. Schmidt et al. 1986. Anal Biochem. 156:213-9.
42. Shoji-Kasai et al. 1992. Science. 256:1821-3.
43. Simpson, L. L. 1981. Pharmacol Rev. 33:155-88.
44. Vician, et al. 1995. Proc Natl Acad Sci USA. 92:2164-8.
45. Walton et al. 1988. J Biol. Chem. 263:2055-63.
46. Zhang et al. 2002. Neuron. 34:599-611.

We claim:

1. A method for reducing botulinum toxin serotype B (BoNT/B) toxicity in a human or non-human animal subject comprising administering to the subject an agent that reduces binding between BoNT/B and a polypeptide that is at least 95% identical to the amino acid sequences selected from the group consisting of amino acids 32-52 of SEQ ID NO:2 (mouse synaptotagmin I botulinum toxin serotype B (BoNT/B)-binding domain), amino acids 33-53 of SEQ ID NO:5 (human synaptotagmin I botulinum toxin serotype B (BoNT/B)-binding domain), amino acids 40-60 of SEQ ID NO:7 (mouse synaptotagmin II botulinum toxin serotype B (BoNT/B)-binding domain), amino acids 40-60 of SEQ ID NO:9 (rat synaptotagmin II botulinum toxin serotype B (BoNT/B)-binding domain), and amino acids 37-57 of SEQ ID NO:10 (human synaptotagmin II botulinum toxin serotype B (BoNT/B)-binding domain).

2. The method of claim 1, wherein the subject is a human subject.

3. The method of claim 1, wherein the agent can compete for binding to BoNT/B with a polypeptide that is at least 95% identical to the amino acid sequences selected from the group consisting of amino acids 32-52 of SEQ ID NO:2 (mouse synaptotagmin I botulinum toxin serotype B (BoNT/B)-binding domain), amino acids 33-53 of SEQ ID NO:5 (human synaptotagmin I botulinum toxin serotype B (BoNT/B)-binding domain), amino acids 40-60 of SEQ ID NO:7 (mouse synaptotagmin II botulinum toxin serotype B (BoNT/B)-binding domain), amino acids 40-60 of SEQ ID NO:9 (rat synaptotagmin II botulinum toxin serotype B (BoNT/B)-binding domain), and amino acids 37-57 of SEQ ID NO:10 (human synaptotagmin II botulinum toxin serotype B (BoNT/B)-binding domain).

4. The method of claim 3, wherein the agent is a polypeptide that is at least 95% identical to the amino acid sequences selected from the group consisting of amino acids 32-79 of SEQ ID NO:2, amino acids 32-79 of SEQ ID NO:4, amino acids 33-80 of SEQ ID NO:5, amino acids 40-60 of SEQ ID NO:7, amino acids 40-60 of SEQ ID NO:9, and amino acids 37-57 of SEQ ID NO:10.

5. The method of claim 4, wherein the polypeptide is selected from the group consisting of amino acids 1-61 of SEQ ID NO:7, amino acids 1-87 of SEQ ID NO:7, amino acids 40-87 of SEQ ID NO:7, amino acids 40-267 of SEQ ID NO:7, amino acids 1-267 of SEQ ID NO:7, [amino acids 1-422 of SEQ ID NO:7,] amino acids 1-61 of SEQ ID NO:9, amino acids 1-87 of SEQ ID NO:9, amino acids 40-87 of SEQ ID NO:9, amino acids 40-267 of SEQ ID NO:9, amino acids 1-267 of SEQ ID NO:9, [amino acids 1-422 of SEQ ID NO:9,] amino acids 1-57 of SEQ ID NO:10, amino acids 1-84 of SEQ ID NO:10, amino acids 37-84 of SEQ ID NO:10, amino acids 37-264 of SEQ ID NO:10, and amino acids 1-264 of SEQ ID NO:10[, and amino acids 1-419 of SEQ ID NO:10].

6. The method of claim 1, wherein the agent can compete with BoNT/B for binding to a polypeptide that is at least 95% identical to the amino acid sequences selected from the group consisting of amino acids 32-52 of SEQ ID NO:2, amino acids 33-53 of SEQ ID NO:5, amino acids 40-60 of SEQ ID NO:7, amino acids 40-60 of SEQ ID NO:9, and amino acids 37-57 of SEQ ID NO:10.

7. The method of claim 6, wherein the agent is an antibody specific to a polypeptide that is at least 95% identical to the amino acid sequences selected from the group consisting of amino acids 32-52 of SEQ ID NO:2, amino acids 33-53 of SEQ ID NO:5, amino acids 40-60 of SEQ ID NO:7, amino acids 40-60 of SEQ ID NO:9, and amino acids 37-57 of SEQ ID NO:10.

8. The method of claim 1, wherein the agent can reduce the expression of at least of one of synaptotagmin I and II in the subject.

9. The method of claim 1, wherein the agent can reduce the binding between gangliosides and a polypeptide that is at least 95% identical to the amino acid sequences selected from the group consisting of amino acids 53-79 of SEQ ID NO:2, amino acids 53-79 of SEQ ID NO:4, amino acids 54-80 of SEQ ID NO:5, amino acids 61-87 of SEQ ID NO:7, amino acids 61-87 of SEQ ID NO:9, and amino acids 58-84 of SEQ ID NO:10.

10. The method of claim 9, wherein the agent can reduce the amount of gangliosides available for binding to a ganglioside domain of at least of one of synaptotagmin I and II in the subject.

11. The method of claim 9, wherein the agent can compete with gangliosides for binding to a polypeptide that is at least 95% identical to the amino acid sequences selected from the group consisting of amino acids 53-79 of SEQ ID NO:2, amino acids 53-79 of SEQ ID NO:4, amino acids 54-80 of SEQ ID NO:5, amino acids 61-87 of SEQ ID NO:7, amino acids 61-87 of SEQ ID NO:9, and amino acids 58-84 of SEQ ID NO:10.

12. The method of claim 11, wherein the agent is an antibody specific to a polypeptide that is at least 95% identical to the amino acid sequences selected from the group consisting of amino acids 53-79 of SEQ ID NO:2, amino acids 53-79 of SEQ ID NO:4, amino acids 54-80 of SEQ ID NO:5, amino acids 61-87 of SEQ ID NO:7, amino acids 61-87 of SEQ ID NO:9, and amino acids 58-84 of SEQ ID NO:10.

13. The method of claim 1, wherein the agent is a dominant negative synaptotagmin I or II.

* * * * *

SEQUENCE LISTING

```
<160> NUMBER OF SEQ ID NOS: 10

<210> SEQ ID NO 1
<211> LENGTH: 2381
<212> TYPE: DNA
<213> ORGANISM: Mus musculus
<220> FEATURE:
<221> NAME/KEY: CDS
<222> LOCATION: (525)..(1790)
<220> FEATURE:
<221> NAME/KEY: misc_feature
<222> LOCATION: (618)..(680)
<223> OTHER INFORMATION: BoNT/B binding domain
<220> FEATURE:
<221> NAME/KEY: misc_feature
<222> LOCATION: (681)..(761)
<223> OTHER INFORMATION: Gangliosides binding domain or transmembrane
      domain

<400> SEQUENCE: 1
accggggcaa gcccccaggg tcctgctcac ccaacagggg gctcaggtcc ccgaagtgtg      60
tgcagggcgg gggcggccag ctgggaccag ctggtggccc tagaaaacct cacccacacc     120
cacacccaca caccccttt gtgttgcagg ctgcccctct gagagcggag gcagcgagag      180
agtactcgtt tgcctcgcac cggtccgcgg tgagagcagc ggggaccaag actcgcacca    240
tctcccggtc ggtcctcgct ccagtttccc tctgaatcct acacttcata tgtagacacc     300
ttactcaact ggcatttgtt agtcaagtct cctctgcatc caaggaaaag aagactttgg     360
cgcgctcgaa caaccaacat aagcagtctg atcagaagac attcaaattg ccgtcccgag     420
agctccagca gaacatctcg ttaagattga agaaggaga ttccaaaagg acaaaaaacc     480
```

```
                                                                              -continued caaatactcc agactacccc cagcagacat ccgctgaacc aaaa atg gtg agt gcc              536
                                                    Met Val Ser Ala
                                                      1 agt cgt cct gag gcc ctg gct gcc cct gtc acc act gtt gcg acc ctt              584
Ser Arg Pro Glu Ala Leu Ala Ala Pro Val Thr Thr Val Ala Thr Leu
  5              10              15              20 gtc cca cac aac gcc act gag cca gcc agt cct ggg gaa ggg aag gaa              632
Val Pro His Asn Ala Thr Glu Pro Ala Ser Pro Gly Glu Gly Lys Glu
             25              30              35 gat gcc ttt tcc aag ctg aag cag aag ttt atg aat gaa ctg cat aaa              680
Asp Ala Phe Ser Lys Leu Lys Gln Lys Phe Met Asn Glu Leu His Lys
             40              45              50 atc cca ttg cca ccg tgg gcc tta att gcc ata gcc ata gtt gcg gtc              728
Ile Pro Leu Pro Pro Trp Ala Leu Ile Ala Ile Ala Ile Val Ala Val
         55              60              65 ctt cta gtc gtg acc tgc tgc ttc tgt gtc tgt aag aaa tgt ttg ttc              776
Leu Leu Val Val Thr Cys Cys Phe Cys Val Cys Lys Lys Cys Leu Phe
 70              75              80 aaa aag aaa aac aag aag aag gga aag gaa aag gga ggg aag aac gcc              824
Lys Lys Lys Asn Lys Lys Lys Gly Lys Glu Lys Gly Gly Lys Asn Ala
85              90              95              100 att aac atg aaa gac gtg aaa gac tta ggg aag acc atg aag gat cag              872
Ile Asn Met Lys Asp Val Lys Asp Leu Gly Lys Thr Met Lys Asp Gln
             105             110             115 gcc ctt aag gat gac gat gct gaa act gga ctg act gat gga gaa gaa              920
Ala Leu Lys Asp Asp Asp Ala Glu Thr Gly Leu Thr Asp Gly Glu Glu
             120             125             130 aag gag gag ccc aag gaa gag gag aaa ctg gga aag ctt caa tat tca              968
Lys Glu Glu Pro Lys Glu Glu Glu Lys Leu Gly Lys Leu Gln Tyr Ser
             135             140             145 ctg gac tat gac ttc cag aat aac cag ctg ctg gtg gga atc atc cag             1016
Leu Asp Tyr Asp Phe Gln Asn Asn Gln Leu Leu Val Gly Ile Ile Gln
     150             155             160 gct gct gaa ctg ccc gcc ctg gac atg gga ggc aca tct gat cca tac             1064
Ala Ala Glu Leu Pro Ala Leu Asp Met Gly Gly Thr Ser Asp Pro Tyr
165             170             175             180 gtc aaa gtc ttc ctg ctg ccc gac aaa aag aag aag ttt gag aca aaa             1112
Val Lys Val Phe Leu Leu Pro Asp Lys Lys Lys Lys Phe Glu Thr Lys
             185             190             195 gtc cac cgg aaa acc ctc aat cca gtc ttc aat gaa cag ttt act ttc             1160
Val His Arg Lys Thr Leu Asn Pro Val Phe Asn Glu Gln Phe Thr Phe
             200             205             210 aag gtg cca tac tcg gaa tta ggt ggc aag aca ctg gtg atg gct gtg             1208
Lys Val Pro Tyr Ser Glu Leu Gly Gly Lys Thr Leu Val Met Ala Val
             215             220             225 tat gat ttt gac cgc ttc tcc aag cac gac atc att gga gag ttc aaa             1256
Tyr Asp Phe Asp Arg Phe Ser Lys His Asp Ile Ile Gly Glu Phe Lys
         230             235             240 gtt cct atg aac acc gtg gat ttt ggc cac gtc acc gag gag tgg cgc             1304
Val Pro Met Asn Thr Val Asp Phe Gly His Val Thr Glu Glu Trp Arg
245             250             255             260 gat ctc cag agt gct gag aaa gaa gag caa gag aaa ctg ggt gac atc             1352
Asp Leu Gln Ser Ala Glu Lys Glu Glu Gln Glu Lys Leu Gly Asp Ile
             265             270             275 tgc ttc tcc ctc cgc tac gtc cct act gcc ggc aag ctg act gtt gtc             1400
Cys Phe Ser Leu Arg Tyr Val Pro Thr Ala Gly Lys Leu Thr Val Val
             280             285             290 att ctg gaa gcc aag aac ctg aag aag atg gat gtg ggt ggc tta tct             1448
Ile Leu Glu Ala Lys Asn Leu Lys Lys Met Asp Val Gly Gly Leu Ser
             295             300             305
```

| | | | | | | | | | | | | | | | |
|---|---|---|---|---|---|---|---|---|---|---|---|---|---|---|---|
| gat | ccc | tat | gta | aag | att | cac | ctg | atg | cag | aac | ggc | aag | aga | ctg | aag | 1496 |
| Asp | Pro | Tyr | Val | Lys | Ile | His | Leu | Met | Gln | Asn | Gly | Lys | Arg | Leu | Lys |
| | 310 | | | | | 315 | | | | | 320 | | | | |

```
gat ccc tat gta aag att cac ctg atg cag aac ggc aag aga ctg aag   1496
Asp Pro Tyr Val Lys Ile His Leu Met Gln Asn Gly Lys Arg Leu Lys
    310                 315                 320 aag aaa aag aca acg att aag aag aac aca ctt aac ccc tac tac aat   1544
Lys Lys Lys Thr Thr Ile Lys Lys Asn Thr Leu Asn Pro Tyr Tyr Asn
325                 330                 335                 340 gag tcc ttc agc ttt gaa gtt ccg ttc gag caa atc cag aaa gtg caa   1592
Glu Ser Phe Ser Phe Glu Val Pro Phe Glu Gln Ile Gln Lys Val Gln
                345                 350                 355 gtg gtg gta act gtt ttg gac tat gac aag att ggc aag aac gac gcc   1640
Val Val Val Thr Val Leu Asp Tyr Asp Lys Ile Gly Lys Asn Asp Ala
            360                 365                 370 atc ggc aaa gtc ttt gtg ggc tac aac agc acc ggc gca gag ctg cga   1688
Ile Gly Lys Val Phe Val Gly Tyr Asn Ser Thr Gly Ala Glu Leu Arg
        375                 380                 385 cac tgg tca gac atg ctg gcc aac ccc cgg cga ccc atc gcc cag tgg   1736
His Trp Ser Asp Met Leu Ala Asn Pro Arg Arg Pro Ile Ala Gln Trp
    390                 395                 400 cac act ctg cag gta gag gag gag gtt gat gcc atg ctg gct gtc aag   1784
His Thr Leu Gln Val Glu Glu Glu Val Asp Ala Met Leu Ala Val Lys
405                 410                 415                 420 aag taa aggggaaaag aagcctttct gcgtctgccc acgtagtgct ctttagccag   1840
Lys tatctgtaaa tacctcagta atatgggtcc tttcagtttc cagccatgca ttcctgatac   1900
aatccagtgg tacttcagat cctgttttaa tttgcacaaa tttaagtgta gaaagcccct   1960
atgcccttca tcataccact gccctccaaa tctactcttc ttttaagcaa tatgatgtgt   2020
agatagagca tgactgaaat gtattgtatc acaccgttgt ataccagt atgctaaaga    2080 tttatttcta gtttgtgtat ttgtatgttg taagcgtttc ctaatctgtg tatatctaga   2140 tgttttttaat aagatgttct atttttaaact atgtaaattg actgagatat aggagaactg  2200
ataatatatt atatggtaaa tatagtatcg tctgcattcc agcaaaaata tcaatttgaa   2260
aggcactagt acagttaaac caacatctta aaggacaact taaacctgaa cttttctattg   2320 aatcctttga gtaccaagat ttgctcacac gacatctttg atgggtgaac ccaattttgt   2380
a                                                                    2381
```

<210> SEQ ID NO 2
<211> LENGTH: 421
<212> TYPE: PRT
<213> ORGANISM: Mus musculus

<400> SEQUENCE: 2

```
Met Val Ser Ala Ser Arg Pro Glu Ala Leu Ala Ala Pro Val Thr Thr
1               5                   10                  15

Val Ala Thr Leu Val Pro His Asn Ala Thr Glu Pro Ala Ser Pro Gly
            20                  25                  30

Glu Gly Lys Glu Asp Ala Phe Ser Lys Leu Lys Gln Lys Phe Met Asn
        35                  40                  45

Glu Leu His Lys Ile Pro Leu Pro Pro Trp Ala Leu Ile Ala Ile Ala
    50                  55                  60

Ile Val Ala Val Leu Leu Val Val Thr Cys Cys Phe Cys Val Cys Lys
65                  70                  75                  80

Lys Cys Leu Phe Lys Lys Lys Asn Lys Lys Gly Lys Glu Lys Gly Gly
                85                  90                  95

Gly Lys Asn Ala Ile Asn Met Lys Asp Val Lys Asp Leu Gly Lys Thr
            100                 105                 110
```

```
Met Lys Asp Gln Ala Leu Lys Asp Asp Asp Ala Glu Thr Gly Leu Thr
        115                 120                 125

Asp Gly Glu Glu Lys Glu Glu Pro Lys Glu Glu Glu Lys Leu Gly Lys
    130                 135                 140
Leu Gln Tyr Ser Leu Asp Tyr Asp Phe Gln Asn Asn Gln Leu Leu Val
145                 150                 155                 160
Gly Ile Ile Gln Ala Ala Glu Leu Pro Ala Leu Asp Met Gly Gly Thr
                165                 170                 175
Ser Asp Pro Tyr Val Lys Val Phe Leu Leu Pro Asp Lys Lys Lys Lys
            180                 185                 190
Phe Glu Thr Lys Val His Arg Lys Thr Leu Asn Pro Val Phe Asn Glu
        195                 200                 205
Gln Phe Thr Phe Lys Val Pro Tyr Ser Glu Leu Gly Gly Lys Thr Leu
    210                 215                 220
Val Met Ala Val Tyr Asp Phe Asp Arg Phe Ser Lys His Asp Ile Ile
225                 230                 235                 240
Gly Glu Phe Lys Val Pro Met Asn Thr Val Asp Phe Gly His Val Thr
                245                 250                 255
Glu Glu Trp Arg Asp Leu Gln Ser Ala Glu Lys Glu Glu Gln Glu Lys
            260                 265                 270
Leu Gly Asp Ile Cys Phe Ser Leu Arg Tyr Val Pro Thr Ala Gly Lys
        275                 280                 285
Leu Thr Val Val Ile Leu Glu Ala Lys Asn Leu Lys Lys Met Asp Val
    290                 295                 300
Gly Gly Leu Ser Asp Pro Tyr Val Lys Ile His Leu Met Gln Asn Gly
305                 310                 315                 320
Lys Arg Leu Lys Lys Lys Lys Thr Thr Ile Lys Lys Asn Thr Leu Asn
                325                 330                 335
Pro Tyr Tyr Asn Glu Ser Phe Ser Phe Glu Val Pro Phe Glu Gln Ile
            340                 345                 350
Gln Lys Val Gln Val Val Val Thr Val Leu Asp Tyr Asp Lys Ile Gly
        355                 360                 365
Lys Asn Asp Ala Ile Gly Lys Val Phe Val Gly Tyr Asn Ser Thr Gly
    370                 375                 380
Ala Glu Leu Arg His Trp Ser Asp Met Leu Ala Asn Pro Arg Arg Pro
385                 390                 395                 400

Ile Ala Gln Trp His Thr Leu Gln Val Glu Glu Glu Val Asp Ala Met
                405                 410                 415
Leu Ala Val Lys Lys
            420
```

<210> SEQ ID NO 3
<211> LENGTH: 4654
<212> TYPE: DNA
<213> ORGANISM: Rattus rattus
<220> FEATURE:
<221> NAME/KEY: CDS
<222> LOCATION: (526)..(1791)
<220> FEATURE:
<221> NAME/KEY: misc_feature
<222> LOCATION: (619)..(681)
<223> OTHER INFORMATION: BoNT/B binding domain
<220> FEATURE:
<221> NAME/KEY: misc_feature
<222> LOCATION: (682)..(762)
<223> OTHER INFORMATION: Gangliosides binding domain or transmembrane domain

<400> SEQUENCE: 3

```
ctctgaccga gttcagcccc cagtgtcttt cctccacctc ctcctgcagc ggcagcatcg    60
gcagttggca gtgggcaact tgaggctgta accagggcaa gccccagggg tcctgctcac   120
ccgacagggg gctcagctcc ccaaagggt gtgtgcaggg cggggcggc cagctgggac     180 cagctggtgg ccctagaaaa cctcacccac acccacacac cccttttgtg ttgcaggctg   240
cccctctgag agcggaggca gcgagagtac tcgcgtgcct cgcaccggtc cgcggtgaga   300
gctgcgggga ccaagactcg caccacctcc cggtcctcgc tccaggaaaa gaagacttga   360
aagtgcttga gcaaccaaca tccgcagtca gatcggaaga ctctgccctg ccatcccca    420 gagcgccacc agaacgtctc attaagattg aagaaagatt ccgagaagaa caaaccccc    480 caaatactcc ataatacct gcagaacatt tcacttgaac caaaa atg gtg agt gcc    537
                                                 Met Val Ser Ala
                                                   1
```

```
agt cat cct gag gcc ctg gcc gcc cct gtc acc act gtt gcg acc ctt    585
Ser His Pro Glu Ala Leu Ala Ala Pro Val Thr Thr Val Ala Thr Leu
  5              10              15              20 gtc cca cac aat gcc act gag cca gcc agt cct ggg gaa ggg aag gaa    633
Val Pro His Asn Ala Thr Glu Pro Ala Ser Pro Gly Glu Gly Lys Glu
                25              30              35 gat gcc ttt tcc aag ctg aag cag aag ttt atg aat gag ctg cat aaa    681
Asp Ala Phe Ser Lys Leu Lys Gln Lys Phe Met Asn Glu Leu His Lys
         40              45              50 att cca ttg cca ccg tgg gcc tta ata gcc ata gcc ata gtt gcg gtc    729
Ile Pro Leu Pro Pro Trp Ala Leu Ile Ala Ile Ala Ile Val Ala Val
     55              60              65 ctt tta gtc gta acc tgc tgc ttt tgt gtc tgt aag aaa tgt ttg ttc    777
Leu Leu Val Val Thr Cys Cys Phe Cys Val Cys Lys Lys Cys Leu Phe
 70              75              80 aaa aag aaa aac aag aag aag ggg aag gaa aag gga gga aag aac gcc    825
Lys Lys Lys Asn Lys Lys Lys Gly Lys Glu Lys Gly Gly Lys Asn Ala
85              90              95             100 att aac atg aaa gac gtg aaa gac tta ggg aag acc atg aag gat cag    873
Ile Asn Met Lys Asp Val Lys Asp Leu Gly Lys Thr Met Lys Asp Gln
            105             110             115 gcc ctt aag gat gac gat gct gaa acc gga ctg act gat gga gaa gaa    921
Ala Leu Lys Asp Asp Asp Ala Glu Thr Gly Leu Thr Asp Gly Glu Glu
        120             125             130 aag gaa gag ccc aag gaa gag gag aaa ctg gga aag ctc caa tat tca    969
Lys Glu Glu Pro Lys Glu Glu Glu Lys Leu Gly Lys Leu Gln Tyr Ser
    135             140             145 ctg gac tat gac ttc cag aat aac cag ctg ttg gtg gga atc atc cag   1017
Leu Asp Tyr Asp Phe Gln Asn Asn Gln Leu Leu Val Gly Ile Ile Gln
150             155             160 gct gct gaa ctg ccc gcc ctg gac atg ggg ggt aca tcc gat cca tac   1065
Ala Ala Glu Leu Pro Ala Leu Asp Met Gly Gly Thr Ser Asp Pro Tyr
165             170             175             180 gtc aaa gtc ttc ctg ctg cct gaa aaa aag aag aaa ttt gag act aaa   1113
Val Lys Val Phe Leu Leu Pro Glu Lys Lys Lys Lys Phe Glu Thr Lys
            185             190             195 gtc cac cgg aaa acc ctc aat cca gtc ttc aat gaa caa ttt act ttc   1161
Val His Arg Lys Thr Leu Asn Pro Val Phe Asn Glu Gln Phe Thr Phe
        200             205             210 aag gta ccc tac tcg gaa tta ggt ggc aaa acc ctg gtg atg gct gtg   1209
Lys Val Pro Tyr Ser Glu Leu Gly Gly Lys Thr Leu Val Met Ala Val
    215             220             225 tat gac ttt gat cgc ttc tcc aag cac gac atc atc gga gag ttc aaa   1257
Tyr Asp Phe Asp Arg Phe Ser Lys His Asp Ile Ile Gly Glu Phe Lys
230             235             240
```

| | | | | | | | | | | | | | | | | |
|---|---|---|---|---|---|---|---|---|---|---|---|---|---|---|---|---|
| gtt | cct | atg | aac | acc | gtg | gat | ttt | ggc | cat | gtg | acc | gag | gag | tgg | cgc | 1305 |
| Val | Pro | Met | Asn | Thr | Val | Asp | Phe | Gly | His | Val | Thr | Glu | Glu | Trp | Arg | |
| 245 | | | | 250 | | | | | 255 | | | | | 260 | | |

| | | | | | | | | | | | | | | | | |
|---|---|---|---|---|---|---|---|---|---|---|---|---|---|---|---|---|
| gat | ctc | cag | agc | gct | gag | aaa | gaa | gag | caa | gag | aaa | ctg | ggt | gac | atc | 1353 |
| Asp | Leu | Gln | Ser | Ala | Glu | Lys | Glu | Glu | Gln | Glu | Lys | Leu | Gly | Asp | Ile | |
| | | | | 265 | | | | | 270 | | | | | 275 | | |

| | | | | | | | | | | | | | | | | |
|---|---|---|---|---|---|---|---|---|---|---|---|---|---|---|---|---|
| tgc | ttc | tcc | ctc | cgc | tac | gtc | cct | act | gcc | ggc | aaa | ctg | act | gtt | gtc | 1401 |
| Cys | Phe | Ser | Leu | Arg | Tyr | Val | Pro | Thr | Ala | Gly | Lys | Leu | Thr | Val | Val | |
| | | | 280 | | | | | 285 | | | | | 290 | | | |

| | | | | | | | | | | | | | | | | |
|---|---|---|---|---|---|---|---|---|---|---|---|---|---|---|---|---|
| att | ctg | gaa | gcc | aag | aac | ctg | aag | aag | atg | gat | gtg | ggt | ggc | tta | tct | 1449 |
| Ile | Leu | Glu | Ala | Lys | Asn | Leu | Lys | Lys | Met | Asp | Val | Gly | Gly | Leu | Ser | |
| | | 295 | | | | | 300 | | | | | 305 | | | | |

| | | | | | | | | | | | | | | | | |
|---|---|---|---|---|---|---|---|---|---|---|---|---|---|---|---|---|
| gat | ccc | tac | gtg | aag | att | cac | ctg | atg | cag | aac | ggt | aag | agg | ctg | aag | 1497 |
| Asp | Pro | Tyr | Val | Lys | Ile | His | Leu | Met | Gln | Asn | Gly | Lys | Arg | Leu | Lys | |
| | 310 | | | | | 315 | | | | | 320 | | | | | |

| | | | | | | | | | | | | | | | | |
|---|---|---|---|---|---|---|---|---|---|---|---|---|---|---|---|---|
| aag | aaa | aag | acg | acg | att | aag | aag | aac | aca | ctc | aac | ccc | tac | tac | aac | 1545 |
| Lys | Lys | Lys | Thr | Thr | Ile | Lys | Lys | Asn | Thr | Leu | Asn | Pro | Tyr | Tyr | Asn | |
| 325 | | | | 330 | | | | | 335 | | | | | 340 | | |

| | | | | | | | | | | | | | | | | |
|---|---|---|---|---|---|---|---|---|---|---|---|---|---|---|---|---|
| gag | tcc | ttc | agc | ttt | gaa | gtt | ccg | ttc | gag | caa | atc | cag | aaa | gtg | caa | 1593 |
| Glu | Ser | Phe | Ser | Phe | Glu | Val | Pro | Phe | Glu | Gln | Ile | Gln | Lys | Val | Gln | |
| | | | | 345 | | | | | 350 | | | | | 355 | | |

| | | | | | | | | | | | | | | | | |
|---|---|---|---|---|---|---|---|---|---|---|---|---|---|---|---|---|
| gtg | gtg | gta | act | gtt | ttg | gac | tat | gac | aag | att | ggc | aag | aac | gac | gcc | 1641 |
| Val | Val | Val | Thr | Val | Leu | Asp | Tyr | Asp | Lys | Ile | Gly | Lys | Asn | Asp | Ala | |
| | | | 360 | | | | | 365 | | | | | 370 | | | |

| | | | | | | | | | | | | | | | | |
|---|---|---|---|---|---|---|---|---|---|---|---|---|---|---|---|---|
| atc | gac | aaa | gtc | ttc | gtt | ggt | tac | aac | agc | act | ggg | gcg | gag | ctg | cga | 1689 |
| Ile | Asp | Lys | Val | Phe | Val | Gly | Tyr | Asn | Ser | Thr | Gly | Ala | Glu | Leu | Arg | |
| | | 375 | | | | | 380 | | | | | 385 | | | | |

| | | | | | | | | | | | | | | | | |
|---|---|---|---|---|---|---|---|---|---|---|---|---|---|---|---|---|
| cac | tgg | tca | gac | atc | ctg | gcc | aac | ccc | cgg | cga | ccc | atc | gca | cag | tgg | 1737 |
| His | Trp | Ser | Asp | Ile | Leu | Ala | Asn | Pro | Arg | Arg | Pro | Ile | Ala | Gln | Trp | |
| | 390 | | | | | 395 | | | | | 400 | | | | | |

| | | | | | | | | | | | | | | | | |
|---|---|---|---|---|---|---|---|---|---|---|---|---|---|---|---|---|
| cac | act | ctg | cag | gta | gag | gag | gag | gtt | gat | gcc | atg | ctg | gct | gtc | aag | 1785 |
| His | Thr | Leu | Gln | Val | Glu | Glu | Glu | Val | Asp | Ala | Met | Leu | Ala | Val | Lys | |
| 405 | | | | 410 | | | | | 415 | | | | | 420 | | |

| | | |
|---|---|---|
| aag taa agggaaaacg aagcctttct gcatctgccc acatagtgct ctttagccag | | 1841 |
| Lys | | |
| tatctgtaaa tacctcagta atatgggtcc ttttggtttc cagccatgca ttcctgatac | | 1901 |
| aatccagtgg tacttcaaat cctgttttaa tttgcacaaa tttaagtgta gaaagccctt | | 1961 |
| atgccctcca tcataccact gccctccaaa tctactcttc ttttaagcaa tatgatgtgt | | 2021 |
| agatagagca tgactgaaat tatgtattgt atcacactgt tgtatatacc agtatgctaa | | 2081 |
| agatttattt ctagtttgtg tatttgtatg ttgtaagcgt ttcctaacct gtgtatatct | | 2141 |
| agatgttttt aataagatgt cctatttttaa actatgtaaa ttgactgaga tatagagctg | | 2201 |
| ataatatatt atatggtaaa tatagtatcg tgtgcattcc agcaaaaata tcaacttgaa | | 2261 |
| aggcactagt acagttaaac caacatctta aaggacaact taaacctgag ctttctattg | | 2321 |
| aatcctttga gtaccaagat tcgctcacac aacacctttg atgggcgaac ccaattttgt | | 2381 |
| agaattcttt cacaggcaaa tagcatgacc tgagcagcat ctgggctgac ctcaaggaag | | 2441 |
| caaagccaca aaccgaaata gcatctgtct gtctgtacct gcaaagccaa agccatgctt | | 2501 |
| cgctcttaca gtcaaggaag caatgaacag gagccaatgc gttcctacca ctgcatctag | | 2561 |
| catagcttca tggtggtgtt ctctgtgtgt gcgtgtgcaa gcgtgaaagt gtatgcacgt | | 2621 |
| gtgtatgtgt ggtgcatgcc tttgtttggg gttagggtgg gggaggagga gctgagggaa | | 2681 |
| gtcagcgttt ctgaaatatt gcctgcctgt ttaaacagaa aattatagct ctccattgtc | | 2741 |
| acatttatat aaaacgtgca acctgggaat tctgatccgg atttcacccc aatattgatt | | 2801 |
| ccaaaaggta ttcgcgtgag actttgtaac aaaatatttt attatacaaa accagattag | | 2861 |

```
aaggaatgca gaatattttt aacgcagcaa tctgtgctta ttccacaaag tgactttgtg   2921
gtaaacagac agtattgtaa ccccacgaaa agacggaata taacagttag ccatagttct   2981
gaatgcactt cgacgaagcc aaaacagaca gctagtgatc tttttatatg ctcttttac    3041 gtgagtttta atttgtcctt taaacaaagg tgaaacaaaa ccaagaacaa gttctcgcaa   3101
actgaagcaa cctcttatgt acactagatg cttgacttag gaggagtttt taaatgttct   3161
caatgttatt ctgtagtaaa tggcactatt atgaagccac tagtcattcc atatgagtct   3221
taaggacggc tctgtgtaac actgtgactg ccccgtgtgc ttagacacgt agtttcctca   3281
gtggatagca ctcaacttac tccgtagtga tattgtaaca atactgccat tccctcttac   3341
tgcactgccc aacatgtgtg tagcacaaac agttctcatt cctaaggacc aattcagaac   3401
tgaacagcta tgcataggac agaaagatac atagaccggg tgtgggagaa cacacagcat   3461
tttgtcaaca ctgtgcacta gtcacatttg tcctgctgcc ggtagacagc cacttcagga   3521
agtgagcctg ctacctaaca ccgcttctag actcttctcc cacttgctat tgtggcccgt   3581
tttcacctcc aggtcacaga gaatggcaac atcctgaagg gagagaccat cttcacatct   3641
accaaaataa aatggaggaa tgctaagcat ggcctcgtgc ttgatcttta ggaattagct   3701
ccgtgttttg gacaaaactc aagagaatcc ccaatagggc tggtggtaga ctttaagcac   3761
ggggtcggct gctcctcctg cacacacaac acaaaagcta cccctggtt gtgattcttc    3821 cctcatgaga gaagaggcaa acccctttgcc cttcactccc atcacagcaa actttcagac  3881
ctagaacaga cacacaggac aaggagcaaa tccttcccta tggatgaaca gcacgtttcc   3941
aacattaaaa ccacagatga taggaaacac atactcatag gtgagttaaa cagcagttta   4001
aacaggagac tcaaatgagg ggctttccta tctaagggat caagtcctac caaagagaag   4061
gaacacctta ataccagac actgacattt aatttcatca tctcccgact tgagttgtac    4121
acaatggaac atttccgagg acgcagctcc gagctgccga actgacatta cttcctgcat   4181
tacaatgata ctagcacatt ctcttgcaac actgccaaca tgggattgtc accatagagt   4241
tagttggtac tatatcattc tcttgtgagc cggtgactgg acctgctttc tgaccaagat   4301
ccatcctctg ataagccaca tgtaccttc tgacaatgca gtgtgaagtc ttagaagctg    4361
atgccctaga aagatcctag ttgcctttgt gtatacttac tgcctgcttg agtgtttcta   4421
tgtgtggatt ttctctgtgt ctggtagaaa tgttggggtg ttttcttctg ccataaggct   4481
tgtgacccgc gagccaattc ccttagctgt actttccctt cattttttga taagtggttt   4541
aaattctgtt tcactttgtg tagtgaaccc catggtagtt ttctgattgt tgttaaaaaa   4601
aatgacttaa catattacat ggacactcaa taaaaatgtt ttatttcctg tta          4654
```

<210> SEQ ID NO 4
<211> LENGTH: 421
<212> TYPE: PRT
<213> ORGANISM: Rattus rattus

<400> SEQUENCE: 4

Met Val Ser Ala Ser His Pro Glu Ala Leu Ala Ala Pro Val Thr Thr
1               5                   10                  15

Val Ala Thr Leu Val Pro His Asn Ala Thr Glu Pro Ala Ser Pro Gly
            20                  25                  30

Glu Gly Lys Glu Asp Ala Phe Ser Lys Leu Lys Gln Lys Phe Met Asn
        35                  40                  45

Glu Leu His Lys Ile Pro Leu Pro Pro Trp Ala Leu Ile Ala Ile Ala
    50                  55                  60

```
Ile Val Ala Val Leu Leu Val Thr Cys Cys Phe Cys Val Cys Lys
 65                  70                  75                  80

Lys Cys Leu Phe Lys Lys Asn Lys Lys Gly Lys Glu Lys Gly
                 85                  90                  95

Gly Lys Asn Ala Ile Asn Met Lys Asp Val Lys Asp Leu Gly Lys Thr
                100                 105                 110

Met Lys Asp Gln Ala Leu Lys Asp Asp Ala Glu Thr Gly Leu Thr
        115                 120                 125

Asp Gly Glu Glu Lys Glu Glu Pro Lys Glu Glu Lys Leu Gly Lys
        130                 135                 140

Leu Gln Tyr Ser Leu Asp Tyr Asp Phe Gln Asn Asn Gln Leu Leu Val
145                 150                 155                 160

Gly Ile Ile Gln Ala Ala Glu Leu Pro Ala Leu Asp Met Gly Gly Thr
                165                 170                 175

Ser Asp Pro Tyr Val Lys Val Phe Leu Leu Pro Glu Lys Lys Lys Lys
                180                 185                 190

Phe Glu Thr Lys Val His Arg Lys Thr Leu Asn Pro Val Phe Asn Glu
                195                 200                 205

Gln Phe Thr Phe Lys Val Pro Tyr Ser Glu Leu Gly Gly Lys Thr Leu
                210                 215                 220

Val Met Ala Val Tyr Asp Phe Asp Arg Phe Ser Lys His Asp Ile Ile
225                 230                 235                 240

Gly Glu Phe Lys Val Pro Met Asn Thr Val Asp Phe Gly His Val Thr
                245                 250                 255

Glu Glu Trp Arg Asp Leu Gln Ser Ala Glu Lys Glu Glu Gln Glu Lys
                260                 265                 270

Leu Gly Asp Ile Cys Phe Ser Leu Arg Tyr Val Pro Thr Ala Gly Lys
                275                 280                 285

Leu Thr Val Val Ile Leu Glu Ala Lys Asn Leu Lys Lys Met Asp Val
                290                 295                 300

Gly Gly Leu Ser Asp Pro Tyr Val Lys Ile His Leu Met Gln Asn Gly
305                 310                 315                 320

Lys Arg Leu Lys Lys Lys Lys Thr Thr Ile Lys Lys Asn Thr Leu Asn
                325                 330                 335

Pro Tyr Tyr Asn Glu Ser Phe Ser Phe Glu Val Pro Phe Glu Gln Ile
                340                 345                 350

Gln Lys Val Gln Val Val Val Thr Val Leu Asp Tyr Asp Lys Ile Gly
                355                 360                 365

Lys Asn Asp Ala Ile Asp Lys Val Phe Val Gly Tyr Asn Ser Thr Gly
                370                 375                 380

Ala Glu Leu Arg His Trp Ser Asp Ile Leu Ala Asn Pro Arg Arg Pro
385                 390                 395                 400

Ile Ala Gln Trp His Thr Leu Gln Val Glu Glu Glu Val Asp Ala Met
                405                 410                 415

Leu Ala Val Lys Lys
                420

<210> SEQ ID NO 5
<211> LENGTH: 422
<212> TYPE: PRT
<213> ORGANISM: Homo sapiens
<220> FEATURE:
<221> NAME/KEY: MISC_FEATURE
<222> LOCATION: (33)..(53)
<223> OTHER INFORMATION: BoNT/B binding domain
<220> FEATURE:
```

<221> NAME/KEY: MISC_FEATURE
<222> LOCATION: (54)..(80)
<223> OTHER INFORMATION: Gangliosides binding domain or transmembrane domain

<400> SEQUENCE: 5

```
Met Val Ser Glu Ser His His Glu Ala Leu Ala Pro Pro Val Thr
1               5                   10                  15

Thr Val Ala Thr Val Leu Pro Ser Asn Ala Thr Glu Pro Ala Ser Pro
                20                  25                  30

Gly Glu Gly Lys Glu Asp Ala Phe Ser Lys Leu Lys Glu Lys Phe Met
            35                  40                  45

Asn Glu Leu His Lys Ile Pro Leu Pro Pro Trp Ala Leu Ile Ala Ile
        50                  55                  60

Ala Ile Val Ala Val Leu Leu Val Leu Thr Cys Cys Phe Cys Ile Cys
65                  70                  75                  80

Lys Lys Cys Leu Phe Lys Lys Asn Lys Lys Gly Lys Glu Lys
                85                  90                  95

Gly Gly Lys Asn Ala Ile Asn Met Lys Asp Val Lys Asp Leu Gly Lys
            100                 105                 110

Thr Met Lys Asp Gln Ala Leu Lys Asp Asp Ala Glu Thr Gly Leu
        115                 120                 125

Thr Asp Gly Glu Glu Lys Glu Glu Pro Lys Glu Glu Glu Lys Leu Gly
130                 135                 140

Lys Leu Gln Tyr Ser Leu Asp Tyr Asp Phe Gln Asn Asn Gln Leu Leu
145                 150                 155                 160

Val Gly Ile Ile Gln Ala Ala Glu Leu Pro Ala Leu Asp Met Gly Gly
                165                 170                 175

Thr Ser Asp Pro Tyr Val Lys Val Phe Leu Leu Pro Asp Lys Lys Lys
            180                 185                 190

Lys Phe Glu Thr Lys Val His Arg Lys Thr Leu Asn Pro Val Phe Asn
        195                 200                 205

Glu Gln Phe Thr Phe Lys Val Pro Tyr Ser Glu Leu Gly Gly Lys Thr
210                 215                 220

Leu Val Met Ala Val Tyr Asp Phe Asp Arg Phe Ser Lys His Asp Ile
225                 230                 235                 240

Ile Gly Glu Phe Lys Val Pro Met Asn Thr Val Asp Phe Gly His Val
                245                 250                 255

Thr Glu Glu Trp Arg Asp Leu Gln Ser Ala Glu Lys Glu Glu Gln Glu
            260                 265                 270

Lys Leu Gly Asp Ile Cys Phe Ser Leu Arg Tyr Val Pro Thr Ala Gly
        275                 280                 285

Lys Leu Thr Val Val Ile Leu Glu Ala Lys Asn Leu Lys Lys Met Asp
290                 295                 300

Val Gly Gly Leu Ser Asp Pro Tyr Val Lys Ile His Leu Met Gln Asn
305                 310                 315                 320

Gly Lys Arg Leu Lys Lys Lys Thr Thr Ile Lys Lys Asn Thr Leu
                325                 330                 335

Asn Pro Tyr Tyr Asn Glu Ser Phe Ser Phe Glu Val Pro Phe Glu Gln
            340                 345                 350

Ile Gln Lys Val Gln Val Val Thr Val Leu Asp Tyr Asp Lys Ile
        355                 360                 365

Gly Lys Asn Asp Ala Ile Gly Lys Val Phe Val Gly Tyr Asn Ser Thr
370                 375                 380

Gly Ala Glu Leu Arg His Trp Ser Asp Met Leu Ala Asn Pro Arg Arg
```

```
385                 390                 395                 400
Pro Ile Ala Gln Trp His Thr Leu Gln Val Glu Glu Val Asp Ala
                405                 410                 415

Met Leu Ala Val Lys Lys
        420

<210> SEQ ID NO 6
<211> LENGTH: 1876
<212> TYPE: DNA
<213> ORGANISM: Mus musculus
<220> FEATURE:
<221> NAME/KEY: CDS
<222> LOCATION: (16)..(1284)
<220> FEATURE:
<221> NAME/KEY: misc_feature
<222> LOCATION: (133)..(195)
<223> OTHER INFORMATION: BoNT/B binding domain
<220> FEATURE:
<221> NAME/KEY: misc_feature
<222> LOCATION: (196)..(276)
<223> OTHER INFORMATION: Gangliosides binding domain or transmembrane
       domain

<400> SEQUENCE: 6
atcccctctg ccacc atg aga aac atc ttc aag agg aac cag gag cca aat         51
               Met Arg Asn Ile Phe Lys Arg Asn Gln Glu Pro Asn
                 1               5                  10 gtg gct ccg gcc acc acc act gcc aca atg ccc ctt gca ccc gtc gca         99
Val Ala Pro Ala Thr Thr Thr Ala Thr Met Pro Leu Ala Pro Val Ala
    15                  20                  25 cct gcc gac aac tct aca gag agc acg ggt cct ggg gag agc caa gaa        147
Pro Ala Asp Asn Ser Thr Glu Ser Thr Gly Pro Gly Glu Ser Gln Glu
 30                  35                  40 gac atg ttc gcc aag ctg aag gag aaa ttc ttc aat gag atc aac aag        195
Asp Met Phe Ala Lys Leu Lys Glu Lys Phe Phe Asn Glu Ile Asn Lys
45                  50                  55                  60 atc ccc ttg ccc ccc tgg gct ctg atc gcc atg gct gtg gtt gct ggc        243
Ile Pro Leu Pro Pro Trp Ala Leu Ile Ala Met Ala Val Val Ala Gly
                65                  70                  75 ctc ctg ctc ctc acc tgt tgc ttc tgc atc tgt aag aag tgc tgc tgc        291
Leu Leu Leu Leu Thr Cys Cys Phe Cys Ile Cys Lys Lys Cys Cys Cys
             80                  85                  90 aag aag aag aag aac aag aag gag aag ggc aaa ggc atg aag aac gcc        339
Lys Lys Lys Lys Asn Lys Lys Glu Lys Gly Lys Gly Met Lys Asn Ala
         95                 100                 105 atg aac atg aag gac atg aaa ggg ggc cag gat gac gat gat gca gag        387
Met Asn Met Lys Asp Met Lys Gly Gly Gln Asp Asp Asp Asp Ala Glu
110                 115                 120 aca ggc ctg act gaa gga gaa ggt gaa ggc gag gag gag aaa gag cca        435
Thr Gly Leu Thr Glu Gly Glu Gly Glu Gly Glu Glu Glu Lys Glu Pro
125                 130                 135                 140 gag aac ctg ggc aaa ttg cag ttt tct ctg gac tat gat ttc cag gcc        483
Glu Asn Leu Gly Lys Leu Gln Phe Ser Leu Asp Tyr Asp Phe Gln Ala
                145                 150                 155 aac cag ctc acc gtg ggt gtc ctg cag gct gcg gaa ctc cca gcc ctg        531
Asn Gln Leu Thr Val Gly Val Leu Gln Ala Ala Glu Leu Pro Ala Leu
            160                 165                 170 gac atg ggt ggc aca tca gac cct tat gtc aaa gtc ttc ctc ctc cca        579
Asp Met Gly Gly Thr Ser Asp Pro Tyr Val Lys Val Phe Leu Leu Pro
        175                 180                 185 gac aag aag aag aaa tat gag act aag gtg cat cgg aag acg ctg aac        627
Asp Lys Lys Lys Lys Tyr Glu Thr Lys Val His Arg Lys Thr Leu Asn
    190                 195                 200
```

| | | |
|---|---|---|
| cca gcc ttc aat gag aca ttc act ttc aag gtg cca tac cag gag tta<br>Pro Ala Phe Asn Glu Thr Phe Thr Phe Lys Val Pro Tyr Gln Glu Leu<br>205 210 215 220 | | 675 |
| gca ggc aag acc ctg gtg atg gca atc tat gac ttt gac cgc ttc tct<br>Ala Gly Lys Thr Leu Val Met Ala Ile Tyr Asp Phe Asp Arg Phe Ser<br>225 230 235 | | 723 |
| aag cat gac atc atc ggg gag gtg aag gta ccc atg aac aca gtg gac<br>Lys His Asp Ile Ile Gly Glu Val Lys Val Pro Met Asn Thr Val Asp<br>240 245 250 | | 771 |
| ctt ggc cag ccc atc gag gaa tgg aga gac cta caa ggc gga gag aag<br>Leu Gly Gln Pro Ile Glu Glu Trp Arg Asp Leu Gln Gly Gly Glu Lys<br>255 260 265 | | 819 |
| gaa gag cca gag aag ttg ggt gac atc tgt acc tcc ttg cgc tac gtg<br>Glu Glu Pro Glu Lys Leu Gly Asp Ile Cys Thr Ser Leu Arg Tyr Val<br>270 275 280 | | 867 |
| ccc aca gct ggg aag ctc acc gtc tgt atc ctg gag gcc aag aac ctg<br>Pro Thr Ala Gly Lys Leu Thr Val Cys Ile Leu Glu Ala Lys Asn Leu<br>285 290 295 300 | | 915 |
| aag aag atg gac gta ggg ggc ctt tca gac ccc tat gtg aag atc cac<br>Lys Lys Met Asp Val Gly Gly Leu Ser Asp Pro Tyr Val Lys Ile His<br>305 310 315 | | 963 |
| ctg atg cag aac ggt aag aga ctc aag aag aag aag acg aca gtg aag<br>Leu Met Gln Asn Gly Lys Arg Leu Lys Lys Lys Thr Thr Val Lys<br>320 325 330 | | 1011 |
| aag aag acc ctg aac ccc tac ttc aac gag tcc ttc agc ttc gag atc<br>Lys Lys Thr Leu Asn Pro Tyr Phe Asn Glu Ser Phe Ser Phe Glu Ile<br>335 340 345 | | 1059 |
| ccc ttt gag cag atc cag aaa gtc cag gtg gtc gtc acc gtg cta gac<br>Pro Phe Glu Gln Ile Gln Lys Val Gln Val Val Val Thr Val Leu Asp<br>350 355 360 | | 1107 |
| tac gac aaa ctg ggc aag aat gaa gcc atc gga aag atc ttt gta ggc<br>Tyr Asp Lys Leu Gly Lys Asn Glu Ala Ile Gly Lys Ile Phe Val Gly<br>365 370 375 380 | | 1155 |
| agc aac gcc aca ggc acc gag ttg cgg cac tgg tcc gac atg ctg gcc<br>Ser Asn Ala Thr Gly Thr Glu Leu Arg His Trp Ser Asp Met Leu Ala<br>385 390 395 | | 1203 |
| aac cct cgg agg ccc att gcc cag tgg cac tct ctt aag cct gag gaa<br>Asn Pro Arg Arg Pro Ile Ala Gln Trp His Ser Leu Lys Pro Glu Glu<br>400 405 410 | | 1251 |
| gaa gtg gat gct ctt ctg ggc aag aac aag tag gctccagcgg ccggtgccac<br>Glu Val Asp Ala Leu Leu Gly Lys Asn Lys<br>415 420 | | 1304 |
| gccctaagg agccacgccc ccgaggcgcc acgcccctg aggacactga cgagatccag | | 1364 |
| agctatcaat acctcagtta cgcgaccta gaggtttctt catttgtttg cggtgtgtcc | | 1424 |
| tgttttccct tccttttct cttttaaag accaacttcc ttttggtggc tgtgtgaaga | | 1484 |
| gagtccccta agaggtgaaa gaaaagcctg gctctgttat tgtccccgga gcggtccttg | | 1544 |
| ttgcatgccc tttcacggtt tccccttac cccaagtggg gccctctact gtcagacagt | | 1604 |
| tgaagcacta actgcttttc ctgggttttg gaccaacaac atggcaagca cattctgttt | | 1664 |
| cttgactgtg aaggcaacat agtggccagc attgtgtgtg tgtgtgtgtg tgtgtgtgtg | | 1724 |
| tatgtgtgtg tgtacacctg tatgtgccca tccatcccca cctgcctgtt ttgaacatct | | 1784 |
| ctcttcattt tctggaatga gtcatggaca gtgaagccat gtgagaggag aatgtcttca | | 1844 |
| gagactccaa gggaaagcaa gcccactgcc tg | | 1876 |

<210> SEQ ID NO 7
<211> LENGTH: 422
<212> TYPE: PRT

<213> ORGANISM: Mus musculus

<400> SEQUENCE: 7

```
Met Arg Asn Ile Phe Lys Arg Asn Gln Glu Pro Asn Val Ala Pro Ala
1               5                   10                  15

Thr Thr Thr Ala Thr Met Pro Leu Ala Pro Val Ala Pro Ala Asp Asn
            20                  25                  30

Ser Thr Glu Ser Thr Gly Pro Gly Glu Ser Gln Glu Asp Met Phe Ala
        35                  40                  45

Lys Leu Lys Glu Lys Phe Phe Asn Glu Ile Asn Lys Ile Pro Leu Pro
    50                  55                  60

Pro Trp Ala Leu Ile Ala Met Ala Val Val Ala Gly Leu Leu Leu Leu
65                  70                  75                  80

Thr Cys Cys Phe Cys Ile Cys Lys Lys Cys Cys Cys Lys Lys Lys Lys
                85                  90                  95

Asn Lys Lys Glu Lys Gly Lys Gly Met Lys Asn Ala Met Asn Met Lys
                100                 105                 110

Asp Met Lys Gly Gly Gln Asp Asp Asp Ala Glu Thr Gly Leu Thr
            115                 120                 125

Glu Gly Glu Gly Glu Gly Glu Glu Lys Glu Pro Glu Asn Leu Gly
130                 135                 140

Lys Leu Gln Phe Ser Leu Asp Tyr Asp Phe Gln Ala Asn Gln Leu Thr
145                 150                 155                 160

Val Gly Val Leu Gln Ala Ala Glu Leu Pro Ala Leu Asp Met Gly Gly
                165                 170                 175

Thr Ser Asp Pro Tyr Val Lys Val Phe Leu Leu Pro Asp Lys Lys Lys
            180                 185                 190

Lys Tyr Glu Thr Lys Val His Arg Lys Thr Leu Asn Pro Ala Phe Asn
        195                 200                 205

Glu Thr Phe Thr Phe Lys Val Pro Tyr Gln Glu Leu Ala Gly Lys Thr
    210                 215                 220

Leu Val Met Ala Ile Tyr Asp Phe Asp Arg Phe Ser Lys His Asp Ile
225                 230                 235                 240

Ile Gly Glu Val Lys Val Pro Met Asn Thr Val Asp Leu Gly Gln Pro
                245                 250                 255

Ile Glu Glu Trp Arg Asp Leu Gln Gly Gly Glu Lys Glu Glu Pro Glu
            260                 265                 270

Lys Leu Gly Asp Ile Cys Thr Ser Leu Arg Tyr Val Pro Thr Ala Gly
        275                 280                 285

Lys Leu Thr Val Cys Ile Leu Glu Ala Lys Asn Leu Lys Lys Met Asp
    290                 295                 300

Val Gly Gly Leu Ser Asp Pro Tyr Val Lys Ile His Leu Met Gln Asn
305                 310                 315                 320

Gly Lys Arg Leu Lys Lys Lys Thr Thr Val Lys Lys Lys Thr Leu
                325                 330                 335

Asn Pro Tyr Phe Asn Glu Ser Phe Ser Phe Glu Ile Pro Phe Glu Gln
            340                 345                 350

Ile Gln Lys Val Gln Val Val Thr Val Leu Asp Tyr Asp Lys Leu
        355                 360                 365

Gly Lys Asn Glu Ala Ile Gly Lys Ile Phe Val Gly Ser Asn Ala Thr
    370                 375                 380

Gly Thr Glu Leu Arg His Trp Ser Asp Met Leu Ala Asn Pro Arg Arg
385                 390                 395                 400

Pro Ile Ala Gln Trp His Ser Leu Lys Pro Glu Glu Glu Val Asp Ala
```

-continued 405 410 415

Leu Leu Gly Lys Asn Lys
420

<210> SEQ ID NO 8
<211> LENGTH: 2681
<212> TYPE: DNA
<213> ORGANISM: Rattus norvegicus
<220> FEATURE:
<221> NAME/KEY: CDS
<222> LOCATION: (115)..(1383)
<220> FEATURE:
<221> NAME/KEY: misc_feature
<222> LOCATION: (232)..(294)
<223> OTHER INFORMATION: BoNT/B binding domain
<220> FEATURE:
<221> NAME/KEY: misc_feature
<222> LOCATION: (295)..(375)
<223> OTHER INFORMATION: Gangliosides binding domain or transmembrane domain

<400> SEQUENCE: 8
gggagccgat cggtgtgggc tggtggagaa ggcagcggga gtctgccgcc ccgaagtcca 60
ggtcccctct tcccactccc gcgccggcca gcgctgcggc tcccctctgc cacc atg 117
Met
1 aga aac atc ttc aag agg aac cag gag ccc att gtg gct ccg gcc acc 165
Arg Asn Ile Phe Lys Arg Asn Gln Glu Pro Ile Val Ala Pro Ala Thr
5 10 15 acc act gcc aca atg cct ctg gca ccc gcc gca cct gcc gat aac tct 213
Thr Thr Ala Thr Met Pro Leu Ala Pro Ala Ala Pro Ala Asp Asn Ser
20 25 30 aca gag agc acg ggc acc ggg gag agc caa gaa gac atg ttc gcc aag 261
Thr Glu Ser Thr Gly Thr Gly Glu Ser Gln Glu Asp Met Phe Ala Lys
35 40 45 ctg aag gac aaa ttc ttc aat gag atc aac aag atc cct ttg ccc ccc 309
Leu Lys Asp Lys Phe Phe Asn Glu Ile Asn Lys Ile Pro Leu Pro Pro
50 55 60 65 tgg gct ctg att gcc atg gcc gtg gtt gct ggc ctc ctg ctg ctc acc 357
Trp Ala Leu Ile Ala Met Ala Val Val Ala Gly Leu Leu Leu Leu Thr
70 75 80 tgc tgc ttc tgc atc tgt aag aag tgc tgc tgc aag aag aag aaa aac 405
Cys Cys Phe Cys Ile Cys Lys Lys Cys Cys Cys Lys Lys Lys Lys Asn
85 90 95 aag aag gag aag ggc aaa ggc atg aag aac gcc atg aac atg aag gac 453
Lys Lys Glu Lys Gly Lys Gly Met Lys Asn Ala Met Asn Met Lys Asp
100 105 110 atg aag ggg ggc cag gat gat gac gac gcg gag aca ggc ctg act gaa 501
Met Lys Gly Gly Gln Asp Asp Asp Asp Ala Glu Thr Gly Leu Thr Glu
115 120 125 gga gaa gga gaa ggc gag gag gag aaa gag ccg gag aac ctg ggc aaa 549
Gly Glu Gly Glu Gly Glu Glu Glu Lys Glu Pro Glu Asn Leu Gly Lys
130 135 140 145 ttg cag ttt tct ctg gac tat gat ttc caa gcc aac cag ctc acc gtg 597
Leu Gln Phe Ser Leu Asp Tyr Asp Phe Gln Ala Asn Gln Leu Thr Val
150 155 160 ggc gtc ctg cag gct gct gaa ctc ccg gcc ctg gac atg ggt ggc acg 645
Gly Val Leu Gln Ala Ala Glu Leu Pro Ala Leu Asp Met Gly Gly Thr
165 170 175 tca gac cct tac gtc aaa gtc ttc ctc ctc cca gac aag aag aag aaa 693
Ser Asp Pro Tyr Val Lys Val Phe Leu Leu Pro Asp Lys Lys Lys Lys
180 185 190 tat gag acc aag gtg cac cgg aag aca ctg aac cca gcc ttc aac gaa 741

```
                Tyr Glu Thr Lys Val His Arg Lys Thr Leu Asn Pro Ala Phe Asn Glu
                    195                 200                 205 act ttc act ttc aag gtg cca tac cag gag tta gga ggc aaa acc ctg      789
Thr Phe Thr Phe Lys Val Pro Tyr Gln Glu Leu Gly Gly Lys Thr Leu
210                 215                 220                 225 gtg atg gct atc tat gac ttt gac cgc ttc tct aag cat gac atc atc      837
Val Met Ala Ile Tyr Asp Phe Asp Arg Phe Ser Lys His Asp Ile Ile
                    230                 235                 240 ggg gag gtg aaa gtg ccc atg aac acg gtg gac ctt ggc cag ccc atc      885
Gly Glu Val Lys Val Pro Met Asn Thr Val Asp Leu Gly Gln Pro Ile
                245                 250                 255 gag gaa tgg aga gac cta caa ggc gga gag aag gaa gag cca gag aag      933
Glu Glu Trp Arg Asp Leu Gln Gly Gly Glu Lys Glu Glu Pro Glu Lys
            260                 265                 270 ctg ggt gac atc tgt acc tcc ttg cgc tac gtg ccc act gct ggg aag      981
Leu Gly Asp Ile Cys Thr Ser Leu Arg Tyr Val Pro Thr Ala Gly Lys
        275                 280                 285 ctc acc gtc tgt atc ctg gag gcc aag aac ctg aag aag atg gat gtg     1029
Leu Thr Val Cys Ile Leu Glu Ala Lys Asn Leu Lys Lys Met Asp Val
290                 295                 300                 305 ggg ggc ctc tca gac ccc tat gtg aag atc cac ttg atg cag aat ggc     1077
Gly Gly Leu Ser Asp Pro Tyr Val Lys Ile His Leu Met Gln Asn Gly
                    310                 315                 320 aag aga ctc aag aag aag aag acg acg gtg aag aag aag acc ttg aac     1125
Lys Arg Leu Lys Lys Lys Lys Thr Thr Val Lys Lys Lys Thr Leu Asn
                325                 330                 335 ccc tac ttc aat gag tca ttc agc ttc gag atc ccc ttt gag cag atc     1173
Pro Tyr Phe Asn Glu Ser Phe Ser Phe Glu Ile Pro Phe Glu Gln Ile
            340                 345                 350 cag aaa gtc cag gtg gtc gtc acc gtg cta gac tat gac aaa ctg ggc     1221
Gln Lys Val Gln Val Val Val Thr Val Leu Asp Tyr Asp Lys Leu Gly
        355                 360                 365 aag aat gaa gcc atc gga aag atc ttc gta ggc agc aac gct aca ggc     1269
Lys Asn Glu Ala Ile Gly Lys Ile Phe Val Gly Ser Asn Ala Thr Gly
370                 375                 380                 385 acg gag ctg cgg cac tgg tcc gac atg ctg gcg aac cct cgg agg ccc     1317
Thr Glu Leu Arg His Trp Ser Asp Met Leu Ala Asn Pro Arg Arg Pro
                    390                 395                 400 atc gcc cag tgg cac tct ctg aag cct gag gaa gaa gtg gat gct ctt     1365
Ile Ala Gln Trp His Ser Leu Lys Pro Glu Glu Glu Val Asp Ala Leu
                405                 410                 415 ctg ggc aag aac aag tag gcagcggcgc tgggggccac gccccagagg            1413
Leu Gly Lys Asn Lys
            420 acactgacga gctccagagc tatcaatacc tcagttatgc gacccttagag gtttcttcat   1473 ttgtttgcgg tgtgtcctgt tttcctttcc tttttctttt tttgtctttt taaaaaccaa   1533 cttcctttg gtggctatgt gaagaggccc ctaagacgtg aaagagaagc ctggctctgt    1593 tattgtccca ggagctgtcc ttgttgcatg ccctatcacg gttgcccctc accccaagtg   1653 gggccctcta ctgtcagagt ggaagcactt cctgcttttc ctgggttttg gaccaacaaa   1713 gtggcaagca cattctgtgt ctcgactgtg tgtgtgtgtg tgtgtgtgtg tgtgtgtgtg   1773 tgtgtgtgtg tgtgtgtgta cacgtgtgcc catccatccc caccttgcct ctgtttggaa   1833 tatctcttcg tttctggaat gagtcacgga caatgatgcc gtgtgagaga ggaaagtctt   1893 caggtactcc gaggtgagga gagcccactg cttaagtggt cagaggccag aagctctcat   1953 agtccttgcg aaaggccatt tggaagacgc aagatgtgat actggatgta ttccgaacta   2013 ggaccaaagg cttgatgcca tcccagactc cctcttgtca gtcatggctt ccccaggagt   2073
```

-continued

```
ggggctttgg gatcattcat gaaaataaac tatttactcg actggtcgga ttcagccagg    2133
gaccgccagc tccaggatgt cattcttgtt gacgacatca aactttgaag aaacagaagt    2193
cccattactc agctctggat ctttgcctcg tccagtggga ggcagatgct tcctccctct    2253
gcagagtaca agcagtgcgt tcatttgcat tcacgcacca tctgcttttg cctctgtttc    2313
ccttttgtg taagtggaaa aataccatct gacgataagt gctttgcaca gagccagaga     2373
cctattagag ggatgcttgg gtgtttagtt cccttgaggt ccaggtaagg aggaggtgtc    2433
aagaagggga gcgttggtgg acagtgacaa gctagacatt gcagagctcc tcacaactcc    2493
tattcctgac cctctggacc ctttgaccct cagtgatggt agccggagta gcccaggcag    2553
accttaggag aggccccgtc cttcccttcc ttagacagtt ttctcagaat gccaggaaac    2613
acagcgcatt catttcagat gggtggtgga gaaaatgtgc taaggtttgc accctatgtt    2673
cggaattc                                                             2681
```

<210> SEQ ID NO 9
<211> LENGTH: 422
<212> TYPE: PRT
<213> ORGANISM: Rattus norvegicus

<400> SEQUENCE: 9

```
Met Arg Asn Ile Phe Lys Arg Asn Gln Glu Pro Ile Val Ala Pro Ala
1               5                   10                  15

Thr Thr Thr Ala Thr Met Pro Leu Ala Pro Ala Ala Pro Ala Asp Asn
            20                  25                  30

Ser Thr Glu Ser Thr Gly Thr Gly Glu Ser Gln Glu Asp Met Phe Ala
        35                  40                  45

Lys Leu Lys Asp Lys Phe Phe Asn Glu Ile Asn Lys Ile Pro Leu Pro
    50                  55                  60

Pro Trp Ala Leu Ile Ala Met Ala Val Val Ala Gly Leu Leu Leu Leu
65                  70                  75                  80

Thr Cys Cys Phe Cys Ile Cys Lys Lys Cys Cys Cys Lys Lys Lys Lys
                85                  90                  95

Asn Lys Lys Glu Lys Gly Lys Gly Met Lys Asn Ala Met Asn Met Lys
            100                 105                 110

Asp Met Lys Gly Gly Gln Asp Asp Asp Ala Glu Thr Gly Leu Thr
            115                 120                 125

Glu Gly Glu Gly Glu Gly Glu Gly Lys Glu Pro Glu Asn Leu Gly
    130                 135                 140

Lys Leu Gln Phe Ser Leu Asp Tyr Asp Phe Gln Ala Asn Gln Leu Thr
145                 150                 155                 160

Val Gly Val Leu Gln Ala Ala Glu Leu Pro Ala Leu Asp Met Gly Gly
                165                 170                 175

Thr Ser Asp Pro Tyr Val Lys Val Phe Leu Leu Pro Asp Lys Lys Lys
            180                 185                 190

Lys Tyr Glu Thr Lys Val His Arg Lys Thr Leu Asn Pro Ala Phe Asn
        195                 200                 205

Glu Thr Phe Thr Phe Lys Val Pro Tyr Gln Glu Leu Gly Gly Lys Thr
    210                 215                 220

Leu Val Met Ala Ile Tyr Asp Phe Asp Arg Phe Ser Lys His Asp Ile
225                 230                 235                 240

Ile Gly Glu Val Lys Val Pro Met Asn Thr Val Asp Leu Gly Gln Pro
                245                 250                 255

Ile Glu Glu Trp Arg Asp Leu Gln Gly Gly Glu Lys Glu Glu Pro Glu
```

```
                    260                 265                 270
Lys Leu Gly Asp Ile Cys Thr Ser Leu Arg Tyr Val Pro Thr Ala Gly
            275                 280                 285
Lys Leu Thr Val Cys Ile Leu Glu Ala Lys Asn Leu Lys Lys Met Asp
            290                 295                 300
Val Gly Gly Leu Ser Asp Pro Tyr Val Lys Ile His Leu Met Gln Asn
305                 310                 315                 320
Gly Lys Arg Leu Lys Lys Lys Thr Thr Val Lys Lys Lys Thr Leu
            325                 330                 335
Asn Pro Tyr Phe Asn Glu Ser Phe Ser Phe Glu Ile Pro Phe Glu Gln
            340                 345                 350
Ile Gln Lys Val Gln Val Val Thr Val Leu Asp Tyr Asp Lys Leu
            355                 360                 365
Gly Lys Asn Glu Ala Ile Gly Lys Ile Phe Val Gly Ser Asn Ala Thr
            370                 375                 380
Gly Thr Glu Leu Arg His Trp Ser Asp Met Leu Ala Asn Pro Arg Arg
385                 390                 395                 400
Pro Ile Ala Gln Trp His Ser Leu Lys Pro Glu Glu Glu Val Asp Ala
                405                 410                 415
Leu Leu Gly Lys Asn Lys
                420

<210> SEQ ID NO 10
<211> LENGTH: 419
<212> TYPE: PRT
<213> ORGANISM: Homo sapiens
<220> FEATURE:
<221> NAME/KEY: MISC_FEATURE
<222> LOCATION: (37)..(57)
<223> OTHER INFORMATION: BoNT/B binding domain
<220> FEATURE:
<221> NAME/KEY: MISC_FEATURE
<222> LOCATION: (58)..(84)
<223> OTH -continued

```
                165                 170                 175
Pro Tyr Val Lys Val Phe Leu Leu Pro Asp Lys Lys Lys Tyr Glu
            180                 185                 190

Thr Lys Val His Arg Lys Thr Leu Asn Pro Ala Phe Asn Glu Thr Phe
            195                 200                 205

Thr Phe Lys Val Pro Tyr Gln Glu Leu Gly Gly Lys Thr Leu Val Met
    210                 215                 220

Ala Ile Tyr Asp Phe Asp Arg Phe Ser Lys His Asp Ile Ile Gly Glu
225                 230                 235                 240

Val Lys Val Pro Met Asn Thr Val Asp Leu Gly Gln Pro Ile Glu Glu
            245                 250                 255

Trp Arg Asp Leu Gln Gly Gly Glu Lys Glu Glu Pro Glu Lys Leu Gly
            260                 265                 270

Asp Ile Cys Thr Ser Leu Arg Tyr Val Pro Thr Ala Gly Lys Leu Thr
            275                 280                 285

Val Cys Ile Leu Glu Ala Lys Asn Leu Lys Lys Met Asp Val Gly Gly
    290                 295                 300

Leu Ser Asp Pro Tyr Gly Lys Ile His Leu Met Gln Asn Gly Lys Arg
305                 310                 315                 320

Leu Lys Lys Lys Thr Thr Val Lys Lys Thr Leu Asn Pro Tyr
            325                 330                 335

Phe Asn Glu Ser Phe Ser Phe Glu Ile Pro Phe Glu Gln Ile Gln Lys
            340                 345                 350

Val Gln Val Val Val Thr Val Leu Asp Tyr Asp Lys Leu Gly Lys Asn
            355                 360                 365

Glu Ala Ile Gly Lys Ile Phe Val Gly Ser Asn Ala Thr Gly Thr Glu
    370                 375                 380

Leu Arg His Trp Ser Asp Met Leu Ala Asn Pro Arg Arg Pro Ile Ala
385                 390                 395                 400

Gln Trp His Ser Leu Lys Pro Glu Glu Glu Val Asp Ala Leu Leu Gly
            405                 410                 415

Lys Asn Lys
```